(12) United States Patent
Folden et al.

(10) Patent No.: US 8,187,466 B2
(45) Date of Patent: *May 29, 2012

(54) SAFETY VENT STRUCTURE FOR EXTRACORPOREAL CIRCUIT

(75) Inventors: Thomas Irvin Folden, Alamo, CA (US); Martin Joseph Crnkovich, Walnut Creek, CA (US); Colin Weaver, Pleasanton, CA (US); Michael Emmanuel Kotsos, Walnut Creek, CA (US); Melvin D. Jensen, West Haven, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/101,500

(22) Filed: May 5, 2011

(65) Prior Publication Data
US 2011/0210054 A1    Sep. 1, 2011

Related U.S. Application Data

(63) Continuation of application No. 12/233,111, filed on Sep. 18, 2008, now Pat. No. 7,938,967.

(60) Provisional application No. 60/973,730, filed on Sep. 19, 2007.

(51) Int. Cl.
*B01D 24/00* (2006.01)
*B01D 11/00* (2006.01)

(52) U.S. Cl. ............ 210/646; 210/645; 210/323.1; 604/321; 604/405

(58) Field of Classification Search .......... None
See application file for complete search history.

(56) References Cited

U.S. PATENT DOCUMENTS

| | | | |
|---|---|---|---|
| 3,946,731 A | 3/1976 | Lichtenstein | |
| 3,982,538 A | 9/1976 | Sharpe | |
| 3,985,135 A | 10/1976 | Carpenter et al. | |
| 4,026,669 A | 5/1977 | Leonard et al. | |
| 4,137,160 A * | 1/1979 | Ebling et al. | 95/259 |
| 4,231,370 A | 11/1980 | Mroz et al. | |
| 4,370,983 A | 2/1983 | Lichtenstein | |

(Continued)

FOREIGN PATENT DOCUMENTS

DE   102005001779   9/2006

(Continued)

OTHER PUBLICATIONS

Gambro®, "Prismaflex™, Anticipating Critical Care needs and taking our innovative response . . . to new heights", © 2004, Gambro Inc., Lakewood, CO, 8 pp.

(Continued)

*Primary Examiner* — Krishnan S Menon
*Assistant Examiner* — Allison M Gionta
(74) *Attorney, Agent, or Firm* — Fish & Richardson P.C.

(57) ABSTRACT

In general, this disclosure relates to extracorporeal fluid circuits. In some aspects, an air-release device for allowing air to be released from a liquid in extracorporeal circuitry includes an elongate chamber having a bottom region and a top region and a fluid entry port and fluid exit port at or near the bottom region. The air release device also includes a vent structure at or near the top region of the elongate chamber that includes a porous material capable of swelling when moistened such that the vent structure can inhibit liquid from escaping the air-release device during use.

23 Claims, 22 Drawing Sheets

U.S. PATENT DOCUMENTS

| | | | |
|---|---|---|---|
| 4,459,139 A * | 7/1984 | vonReis et al. | 96/6 |
| 4,488,961 A | 12/1984 | Spencer | |
| 4,590,227 A * | 5/1986 | Nakamura et al. | 523/130 |
| 4,643,713 A | 2/1987 | Viitala | |
| 4,662,906 A | 5/1987 | Matkovich et al. | |
| 4,702,675 A | 10/1987 | Aldrovandi et al. | |
| 4,888,004 A | 12/1989 | Williamson | |
| 4,997,464 A | 3/1991 | Kopf | |
| 5,061,236 A | 10/1991 | Sutherland et al. | |
| 5,330,425 A | 7/1994 | Utterberg | |
| 5,441,636 A | 8/1995 | Chevallet et al. | |
| 5,498,338 A | 3/1996 | Kruger | |
| 5,540,265 A | 7/1996 | Polaschegg | |
| 5,578,070 A | 11/1996 | Utterberg | |
| 5,614,677 A | 3/1997 | Wamsiedler et al. | |
| 5,628,908 A | 5/1997 | Kamen et al. | |
| 5,643,205 A | 7/1997 | Utterberg | |
| 5,711,883 A | 1/1998 | Folden et al. | |
| 5,849,065 A | 12/1998 | Wojke | |
| 5,863,421 A | 1/1999 | Peter | |
| 5,928,177 A | 7/1999 | Brugger et al. | |
| 5,989,423 A | 11/1999 | Kamen et al. | |
| 6,179,801 B1 | 1/2001 | Holmes et al. | |
| 6,196,987 B1 | 3/2001 | Holmes et al. | |
| 6,200,287 B1 | 3/2001 | Keller et al. | |
| 6,231,537 B1 | 5/2001 | Holmes et al. | |
| 6,234,989 B1 | 5/2001 | Brierton et al. | |
| 6,280,406 B1 | 8/2001 | Dolecek et al. | |
| 6,336,916 B1 | 1/2002 | Bormann et al. | |
| 6,337,049 B1 | 1/2002 | Tamari | |
| 6,361,518 B1 | 3/2002 | Brierton et al. | |
| 6,383,158 B1 | 5/2002 | Utterberg et al. | |
| 6,409,696 B1 | 6/2002 | Toavs et al. | |
| 6,497,674 B1 | 12/2002 | Steele et al. | |
| 6,514,225 B1 | 2/2003 | Utterberg et al. | |
| 6,536,278 B1 | 3/2003 | Scagliarini | |
| 6,725,726 B1 | 4/2004 | Adolfs et al. | |
| 6,730,055 B2 | 5/2004 | Bainbridge et al. | |
| 6,755,801 B2 | 6/2004 | Utterberg et al. | |
| 6,764,460 B2 | 7/2004 | Dolecek et al. | |
| 6,790,195 B2 | 9/2004 | Steele et al. | |
| 6,852,090 B2 | 2/2005 | Burbank et al. | |
| 6,887,214 B1 | 5/2005 | Levin et al. | |
| 7,021,148 B2 | 4/2006 | Kuhn et al. | |
| 7,115,107 B2 | 10/2006 | Delnevo et al. | |
| 7,517,387 B2 | 4/2009 | Chevallet et al. | |
| 7,603,907 B2 | 10/2009 | Reiter et al. | |
| 7,621,983 B2 | 11/2009 | Neri | |
| 7,892,331 B2 | 2/2011 | Childers et al. | |
| 7,892,332 B2 | 2/2011 | Prisco et al. | |
| 2002/0014462 A1 | 2/2002 | Muller | |
| 2002/0072718 A1 | 6/2002 | Brugger et al. | |
| 2002/0179527 A1 * | 12/2002 | Yao | 210/634 |
| 2004/0019312 A1 * | 1/2004 | Childers et al. | 604/4.01 |
| 2004/0238416 A1 | 12/2004 | Burbank et al. | |
| 2005/0054968 A1 | 3/2005 | Giannella | |
| 2005/0132826 A1 | 6/2005 | Teugels | |
| 2005/0230292 A1 | 10/2005 | Beden et al. | |
| 2007/0086924 A1 | 4/2007 | Moses | |
| 2007/0193940 A1 | 8/2007 | Duchamp et al. | |
| 2007/0269340 A1 | 11/2007 | Dannenmaier et al. | |
| 2008/0275361 A1 | 11/2008 | Loriga et al. | |
| 2009/0216211 A1 | 8/2009 | Beden et al. | |
| 2010/0292627 A1 | 11/2010 | Caleffi et al. | |

FOREIGN PATENT DOCUMENTS

| | | |
|---|---|---|
| EP | 0278100 | 8/1988 |
| EP | 0 327 136 | 8/1989 |
| EP | 0458041 | 11/1991 |
| EP | 0 728 509 | 8/1996 |
| EP | 1 529 545 | 5/2005 |
| EP | 1 547 630 | 6/2005 |
| EP | 1 728 526 | 3/2008 |
| EP | 1 894 587 | 3/2008 |
| EP | 2 226 087 | 9/2010 |
| JP | 2003-180834 | 7/2003 |
| JP | 2005-530543 | 10/2005 |
| WO | WO 9702056 | 1/1997 |
| WO | WO 0108722 | 2/2001 |
| WO | WO 2001/50949 | 7/2001 |
| WO | WO 0164312 | 9/2001 |
| WO | WO 2004/000391 | 12/2003 |
| WO | WO 2005/044340 | 5/2005 |
| WO | WO 2005/044341 | 5/2005 |
| WO | WO 2005077490 | 8/2005 |
| WO | WO 2007/050211 | 5/2007 |
| WO | WO 2008/002370 | 1/2008 |

OTHER PUBLICATIONS

Gambro®, "DEHP-Free Cartridge Blood Sets", © Nov. 2004, Gambro, Inc, Lakewood, CO, 4 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Gambro®, "Prisma® HF 1000, For Increased Filtration Capacity", © Aug. 2001, Gambro Renal Products, Inc., Lakewood, CO, 2 pp.

International Search Report and Written Opinion; PCT/US06/36802; mailed May 8, 2008, 8 pages.

International Search Report and Written Opinion; PCT/US2008/076830; mailed Dec. 29, 2008, 19 pages.

Manns, Markus et al., "The acu-men: A new device for continuous renal replacement therapy in acute renal failure," Kidney International, vol. 54, pp. 268-274, 1998.

* cited by examiner

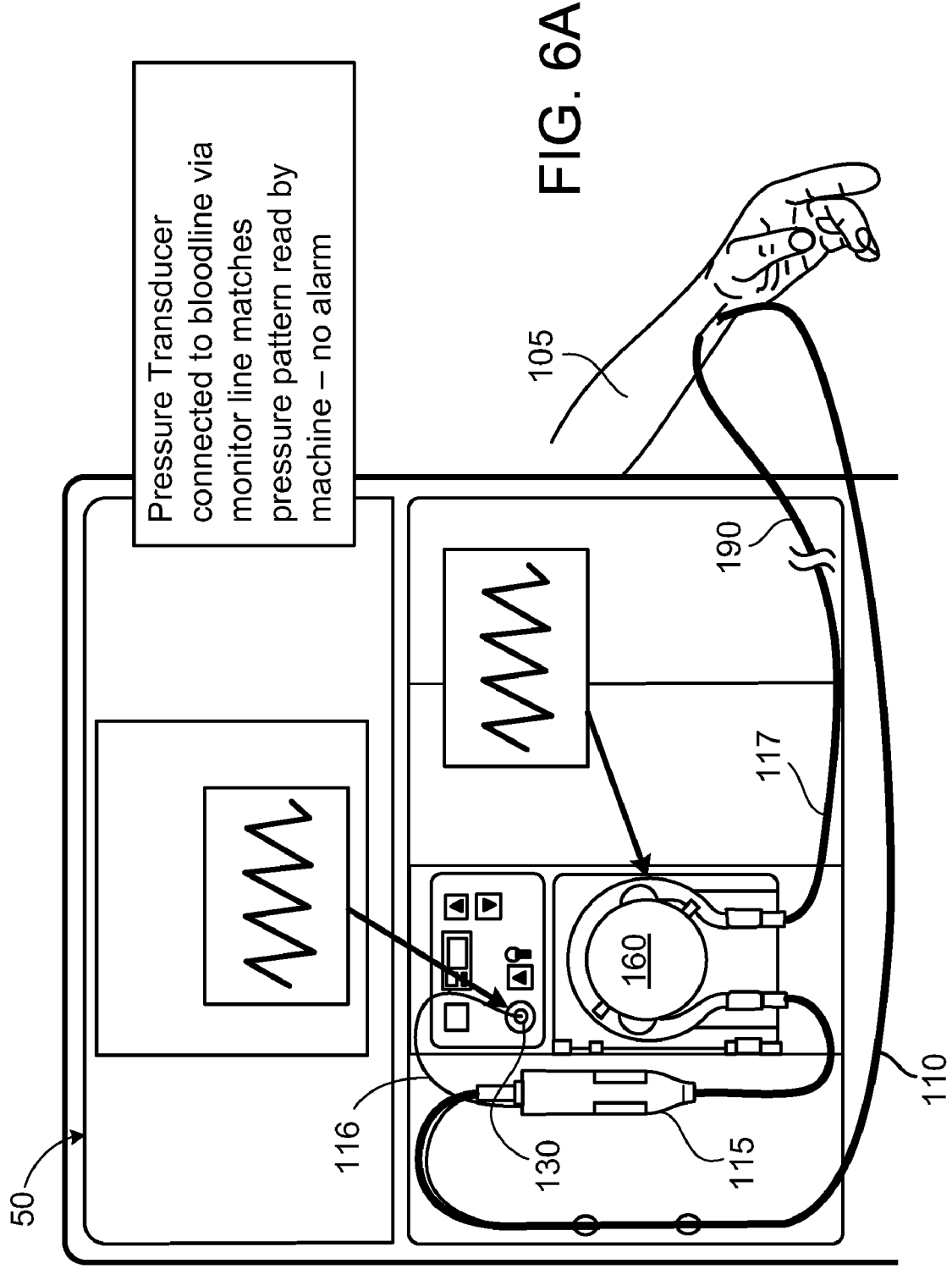

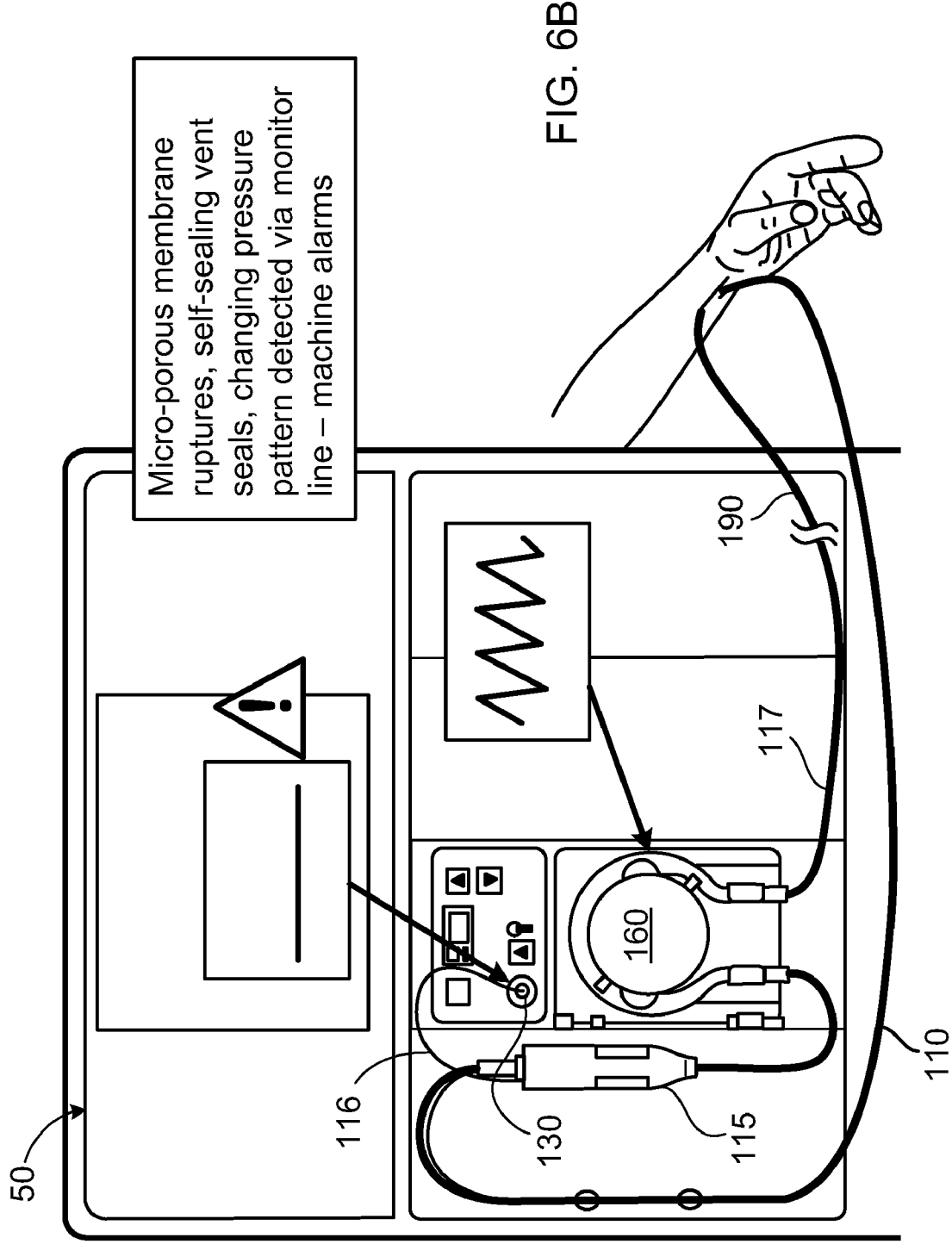

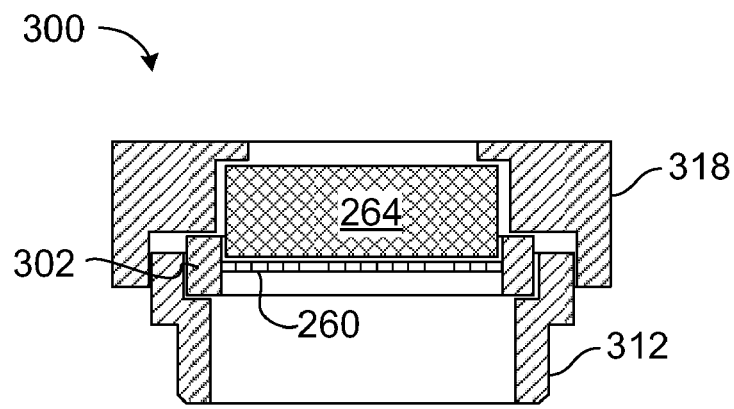
FIG. 12
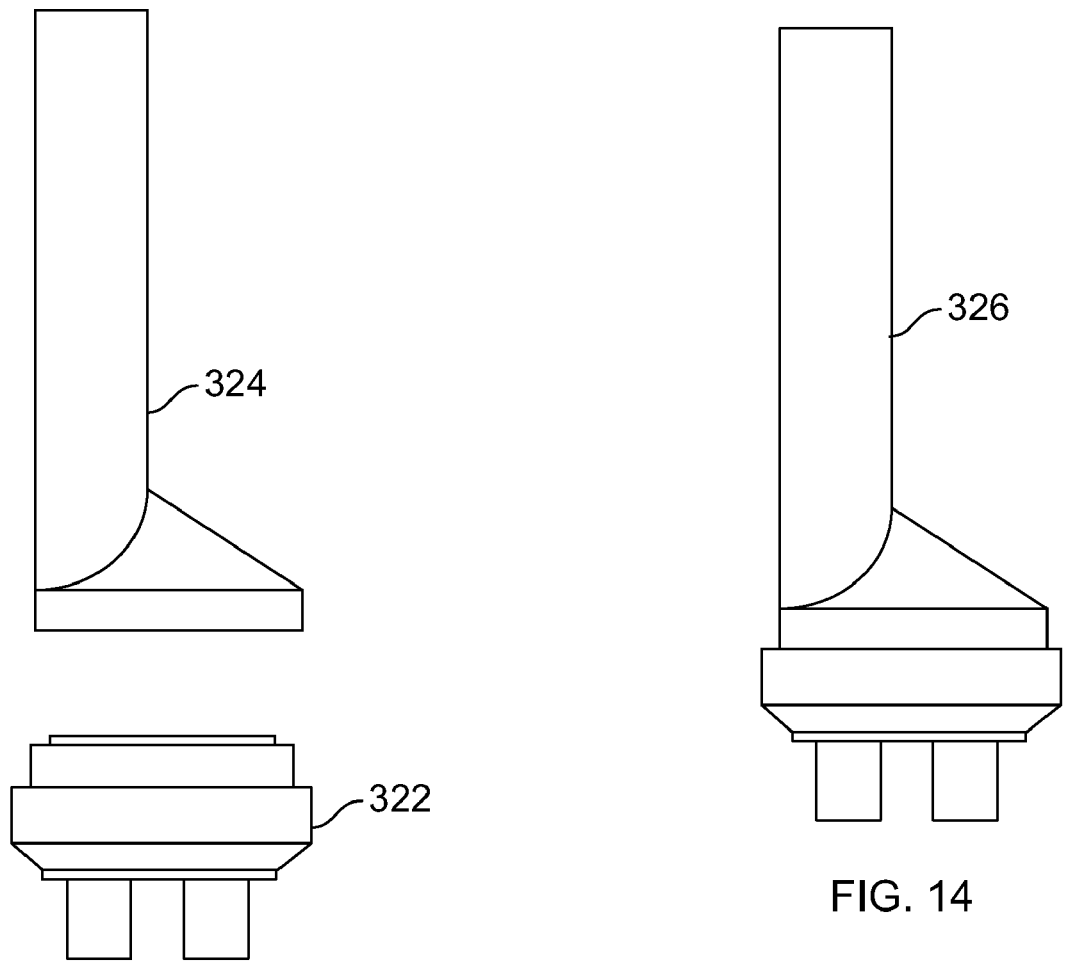
FIG. 13
FIG. 14

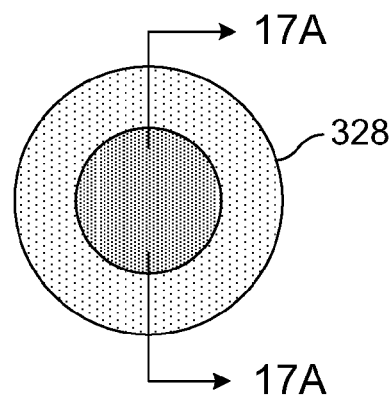
FIG. 17
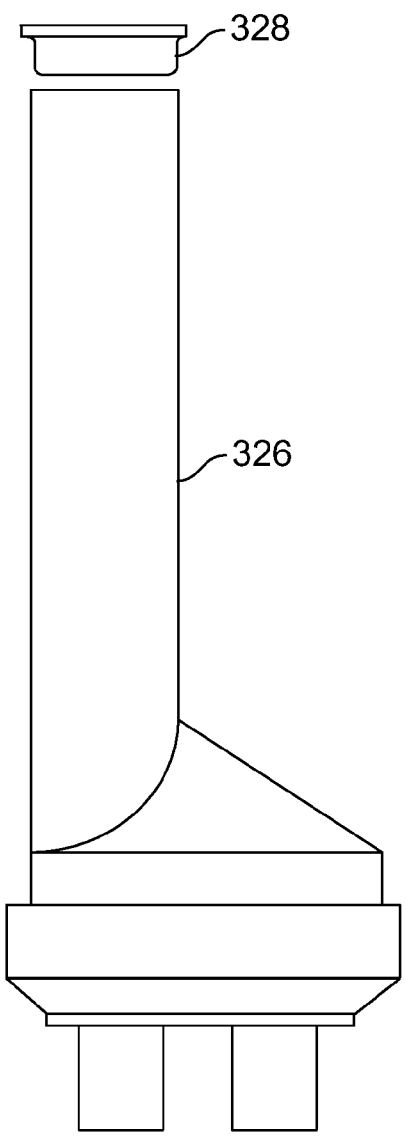
FIG. 19
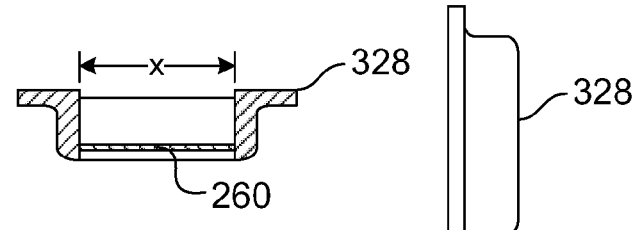
FIG. 17A
FIG. 17B
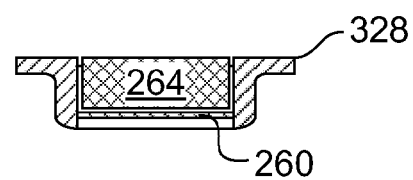
FIG. 18

SAFETY VENT STRUCTURE FOR EXTRACORPOREAL CIRCUIT

CROSS-REFERENCE TO RELATED APPLICATIONS

This application is a continuation application and claims priority to U.S. application Ser. No. 12/233,111, filed Sep. 18, 2008, which claims the benefit of the filing date of U.S. Provisional Application No. 60/973,730, filed Sep. 19, 2007. The contents of U.S. application Ser. Nos. 12/233,111 and 60/973,730 are incorporated by reference herein.

TECHNICAL FIELD

This disclosure relates to extracorporeal fluid circuits.

BACKGROUND

Hemodialysis removes toxic substances and metabolic waste from the bloodstream using an extracorporeal circuit with components designed to perform ultrafiltration and diffusion on the blood. Before the blood is returned to the body, air bubbles are removed from the blood to inhibit embolisms.

SUMMARY

In one aspect, an extracorporeal medical fluid circuit component is described. The component includes a vent assembly. A vent structure adjacent to a micro-porous membrane forms the assembly. The vent structure is porous, but expands when the vent structure becomes wet, thereby closing off the pores and inhibiting (e.g., preventing) fluid from flowing through the vent structure. The vent structure also protects the membrane from becoming wet, such as from condensation. The component is capable of being used in an extracorporeal medical fluid circuit.

In another aspect, a transducer protector includes a body that defines a fluid pathway. A vent assembly is disposed in the fluid pathway. The vent assembly includes a vent structure and a micro-porous membrane. The vent structure is porous, but expands when the vent structure becomes wet, thereby closing off the pores and inhibiting (e.g., preventing) fluid from flowing through the vent structure. The vent structure also protects the membrane from becoming wet, such as from condensation. The transducer protector is capable of being connected in fluid communication with a fluid circuit and a pressure transducer such that the vent assembly inhibits liquid flowing in the fluid circuit from contacting the pressure transducer.

In a further aspect, an extracorporeal medical fluid circuit apparatus, e.g., for removing air from a bodily liquid in extracorporeal circuitry used in a hemodialysis machine, is described. The apparatus includes a chamber having a fluid entry port, a fluid exit port, and a vent assembly. The vent assembly includes a micro-porous membrane and a vent structure adjacent to the micro-porous membrane. The vent structure includes a porous material that is capable of swelling when moistened. The fluid entry port and the fluid exit port are arranged to allow liquid to pass through the chamber from the entry port to the exit port so as to fill the chamber with the liquid when back pressure is applied, and the vent assembly is arranged to allow gas to exit the chamber as the liquid passes through the chamber.

In yet another aspect, an integrated fluid circuit component adapted to removably seat in a dialysis machine is described. The component includes a rigid body having a substantially flat main portion and a plurality of recessed portions extending from the flat main portion and a flexible backing covering at least one of the of recessed portions. A first recessed portion of the plurality of recessed portions forms a chamber. A second recessed portion of the plurality of recessed portions forms a first channel that is in fluid communication with the chamber, and a third recessed portion of the plurality of recessed portions forms a second channel in fluid communication with the chamber. The component also includes a vent assembly that is in fluid communication with the chamber. The vent assembly includes a micro-porous membrane and a vent structure.

In yet another aspect, a dialysis system is described. The system includes a machine body, a pump on the machine body, and fluid circuitry (e.g., tubes) in fluid communication with the pump. The pump is configured to push fluid through the circuitry. The system also includes a vent assembly in fluid communication with the fluid circuitry. The vent assembly includes a micro-porous membrane and a vent structure adjacent to the micro-porous membrane. The vent structure includes a porous material that is capable of swelling when moistened.

In another aspect, a method of removing air from a bodily liquid in dialysis circuitry is described. A chamber with an entry port, an exit port, a micro-porous membrane and a vent structure is provided. A first liquid is passed through the entry port, filling the chamber so that substantially no air remains in the chamber. A second liquid is passed through the entry port, forcing a portion of the first liquid out of an exit port of the chamber and forming a liquid-liquid interface between the first and second liquids. Any gas bubbles contained in the second liquid can be forced out of the chamber through the micro-porous membrane and the vent structure.

Embodiments of the disclosed methods, systems and devices may include one or more of the following features.

The vent structure can have an average pore size of about 15 microns to about 45 microns.

The vent structure can include a polymer such as polyethylene (e.g., high density polyethylene (HDPE)), polypropylene, or polystyrene.

The vent structure can include a swelling agent such as carboxymethylcellulose (CMC), methyl-ethyl-cellulose or other similar swelling agents.

The vent structure can include a blend of a polymer and a swelling agent.

The vent structure can have a thickness greater than a thickness of the micro-porous membrane.

The micro-porous membrane can have an average pore size of about 0.05 microns to about 0.45 microns (e.g., about 0.22 microns or about 0.2 microns).

The micro-porous membrane can be held by a plastic ring (e.g., by insert molding, heat welding, ultrasonic welding, adhesive, clamping, etc.) and the assembly can also include an insert for holding the micro-porous membrane adjacent to the vent structure.

In some embodiments, a structure or assembly can include a plastic ring into which the micro-porous membrane is press-fit, wherein the ring surrounds the vent structure and retains the vent structure adjacent to the micro-porous membrane.

The vent structure can include a first porous layer adjacent to the micro-porous membrane, and a second porous layer adjacent to the first porous layer.

The second porous layer can include a porous material that is capable of swelling when moistened.

The first porous layer can also include a porous material that is capable of swelling when moistened.

The second porous layer can have a greater propensity to swell in the presence of moisture than the first porous layer.

The second porous layer can have an average pore size that is greater than an average pore size of the first porous layer. For example, the first porous layer can have an average pore size of about 10 microns, and the second porous layer can have an average pore size of about 30 microns.

The second porous layer can include about 5% to about 50% by weight carboxymethylcellulose (e.g., about 10% by weight carboxymethylcellulose).

The first porous layer can include 0% to about 10% by weight carboxymethylcellulose (e.g., less than 5% by weight carboxymethylcellulose).

The extracorporeal medical fluid circuit component can be configured for use in an air release chamber.

The extracorporeal medical fluid circuit component can be configured for use in a transducer protector.

The extracorporeal medical fluid circuit component can be configured for use in a blood circuit. The blood circuit can be capable of being used with a dialysis machine.

The micro-porous membrane can be between the vent structure and the chamber.

The vent structure can include porous material that is capable of swelling when moistened.

The dialysis system can include a pressure transducer and a transducer protector that includes the vent assembly.

The transducer protector can be disposed between, and in fluid communication with, the circuitry and the pressure transducer.

Passing the second liquid through the entry port can include passing moisture from the second liquid through the micro-porous membrane and allowing the moisture to pass through the vent structure, causing the vent structure to swell.

Other aspects, features, and advantages are in the description, drawings, and claims.

DESCRIPTION OF DRAWINGS

FIGS. 6A and 6B illustrate a dialysis machine measuring pressure patterns of an extracorporeal blood circuit.

FIG. 12 is a schematic cross-sectional view of a vent assembly.

FIG. 13 is a schematic side view of a chamber and port cap than can be assembled to form a bottom entry/bottom exit chamber.

FIG. 14 is a schematic side view of a bottom entry/bottom exit chamber.

FIG. 17 is a schematic top view of a filter assembly.

FIG. 17A is a cross-sectional view of the filter assembly of FIG. 17, taken along line 17A-17A.

FIG. 17B is a side view of the filter assembly of FIG. 17.

FIG. 18 is a schematic cross-sectional view of a vent assembly.

FIG. 19 is a schematic side view of a bottom entry/bottom exit chamber and a vent assembly.

FIG. 26A is a cross sectional view of the integrated extracorporeal circuit of FIG. 26, take along line 26A-26A.

DETAILED DESCRIPTION

A fluid circuit, such as an extracorporeal fluid circuit used in filtering blood from a patient during hemodialysis, can be provided with one or more self-sealing vent assemblies to inhibit (e.g., prevent) fluids flowing within the circuit from coming into contact with the surrounding, external atmosphere and/or coming into contact with, and possibly contaminating, neighboring devices. The self-sealing vent assemblies can also inhibit (e.g., prevent) foreign particles and organisms from the external atmosphere from coming into contact with liquid flowing within the fluid circuit.

System Overview

Figure 1:
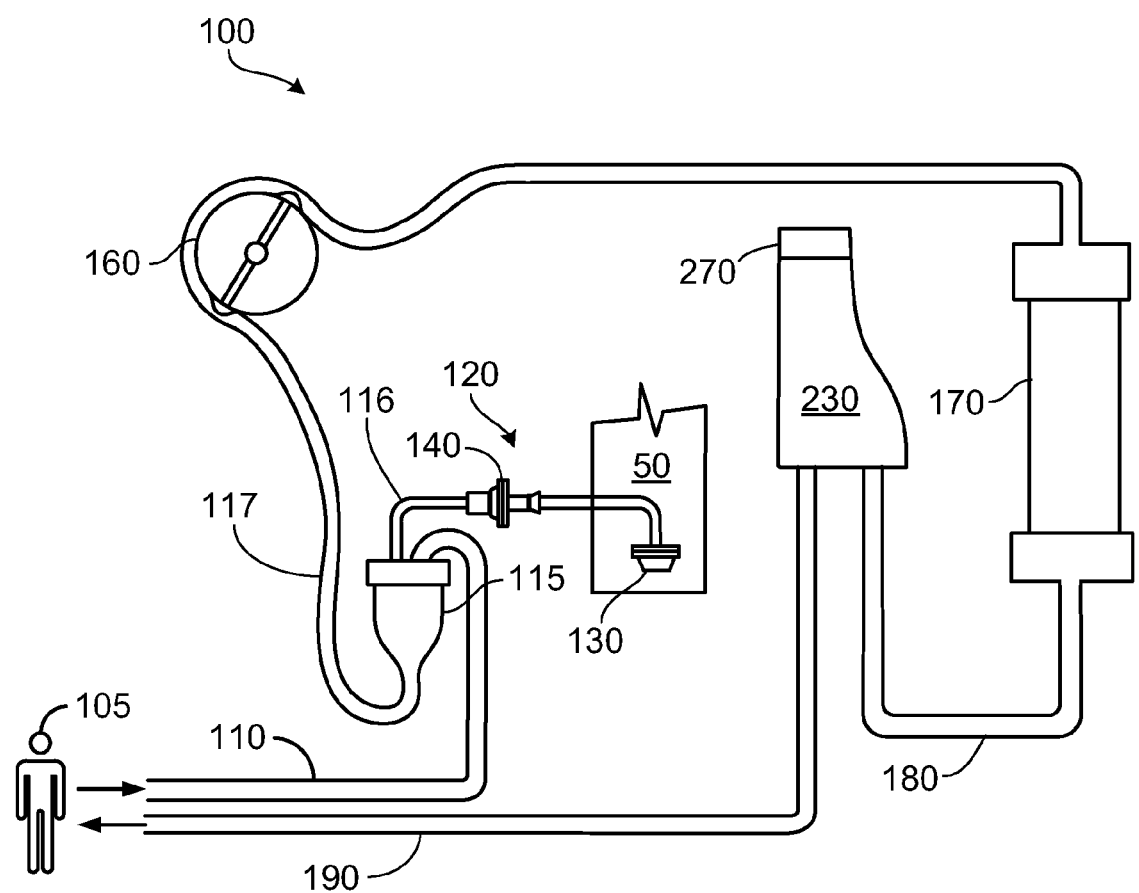
FIG. 1 is a schematic diagram of an extracorporeal fluid circuit for hemodialysis system.
Figure 3A:
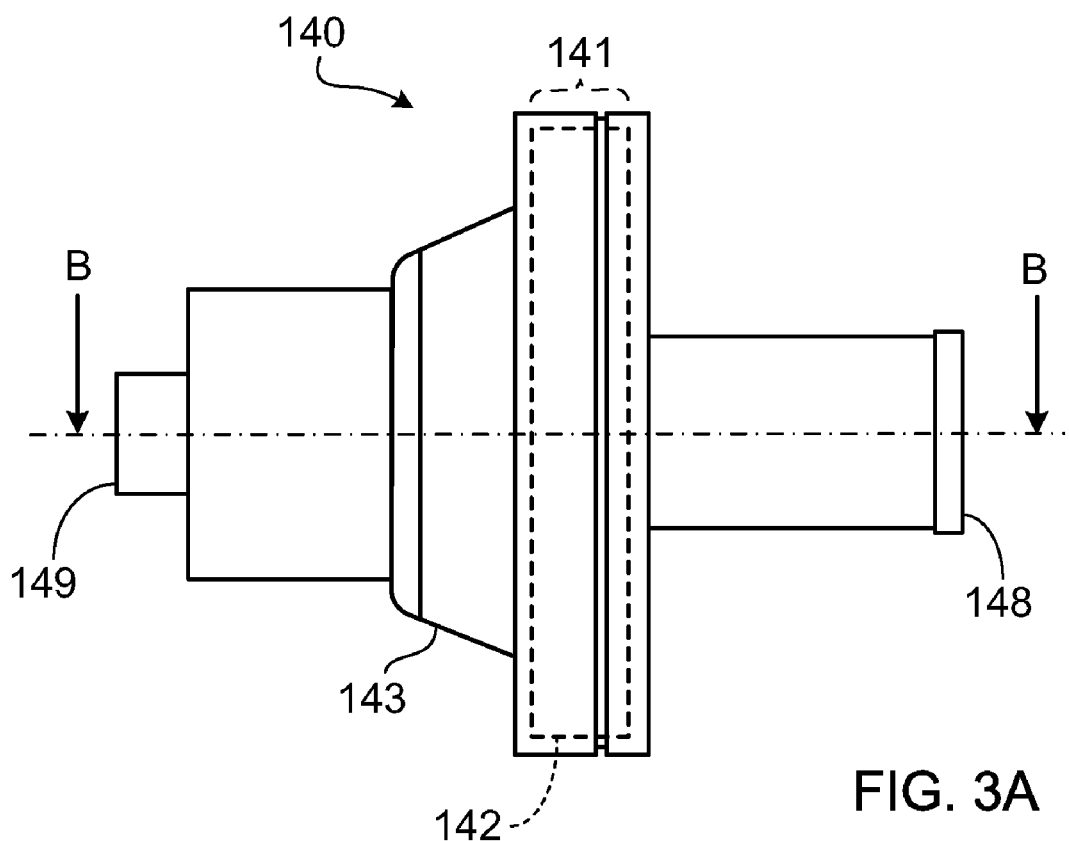
FIG. 3A is side view of a transducer protector.
Figure 3B:
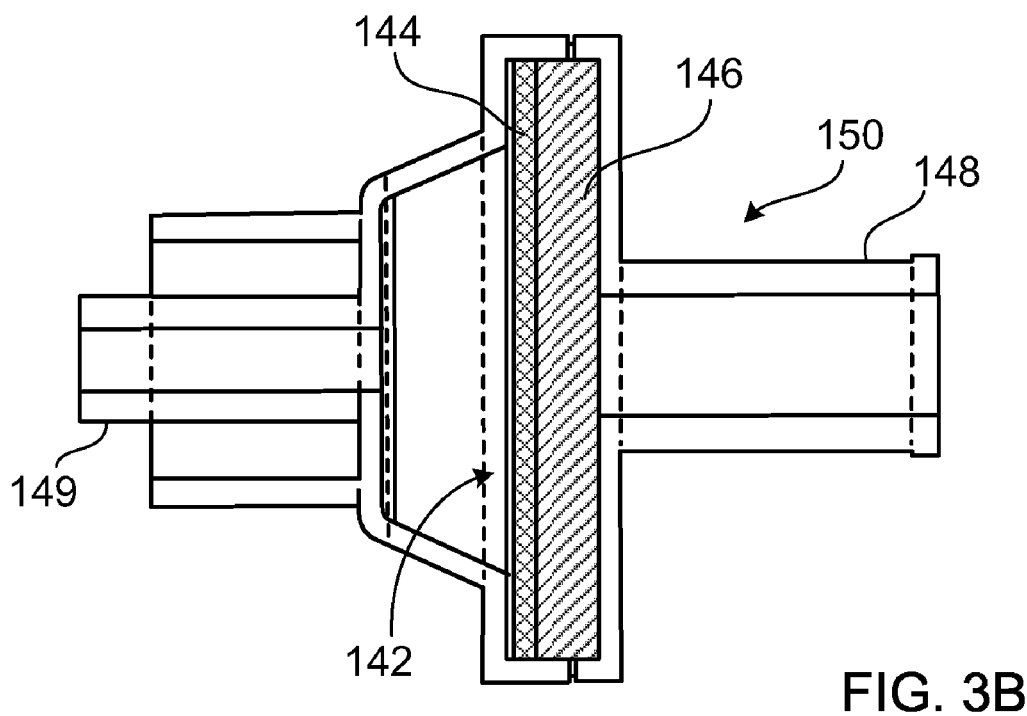
FIG. 3B is a cross-sectional side view of the transducer protector of FIG. 3A.

Referring to FIG. 1, an extracorporeal circuit 100 includes tubing through which the blood flows and components for filtering and performing dialysis on the blood. Blood flows from a patient 105 through arterial tubing 110. Blood drips into a drip chamber 115 where a connecting tube 116 from the drip chamber 115 attaches to an arterial pressure sensor assembly 120 on a hemodialysis machine 50 that determines the pressure of the blood on the arterial side of the circuit 100. The arterial pressure sensor assembly 120 includes a pressure transducer 130, which can be mounted within a dialysis machine 50, so that the pressure of blood flowing through the circuit 100 on the arterial side can be monitored. The arterial pressure sensor assembly 120 also includes a transducer protector 140, which carries a self-sealing vent assembly 141 (FIG. 3B) that includes a micro-porous membrane 144 (FIG. 3B) and a liquid activated self-sealing vent structure 146 (FIG. 3B). The vent assembly 141 helps to protect the pressure transducer 130, and the dialysis machine 50 in which it is mounted, from direct contact with blood flowing within the extracorporeal circuit 100. In the event that the micro-porous membrane 144 ruptures, blood will come into contact with the liquid activated self-sealing vent structure 146. The vent structure 146 will seal, and, by sealing, will inhibit (e.g., prevent) the dialysis machine 50 from becoming contaminated, and will allow the machine 50 to detect a failure via analysis of pressure patterns.

A pump 160, such as a peristaltic pump, forces the blood to continue along the path through the circuit 100. The blood then flows to a dialyzer 170, which separates waste products from the blood.

After passing through the dialyzer 170, the blood flows through venous tubing 180 towards an air release chamber 230 in which gas (e.g., air) in the blood can escape before the blood continues to the patient 105. During treatment, should air be present in the blood, the blood with air bubbles flows in through the bottom of the air release chamber 230. The upper motion of the blood is impeded by gravity and becomes stagnant, while the air continues to the top of the chamber 230 where it is vented out to the atmosphere through another self-sealing vent assembly 270. The vent assembly 270 of the chamber 230 includes a micro-porous membrane and a self-sealing vent. The micro-porous membrane normally operates to inhibit liquids within the chamber from coming into contact with the atmosphere. However, in the event that the micro-porous membrane ruptures, liquid will come into contact with the self-sealing vent, which will self seal and inhibit (e.g., prevent) the blood from coming into contact with the atmosphere.

After leaving the chamber 230, the blood travels through a venous line 190 and back to the patient 105.

Pressure Transducer Assembly

Figure 2:
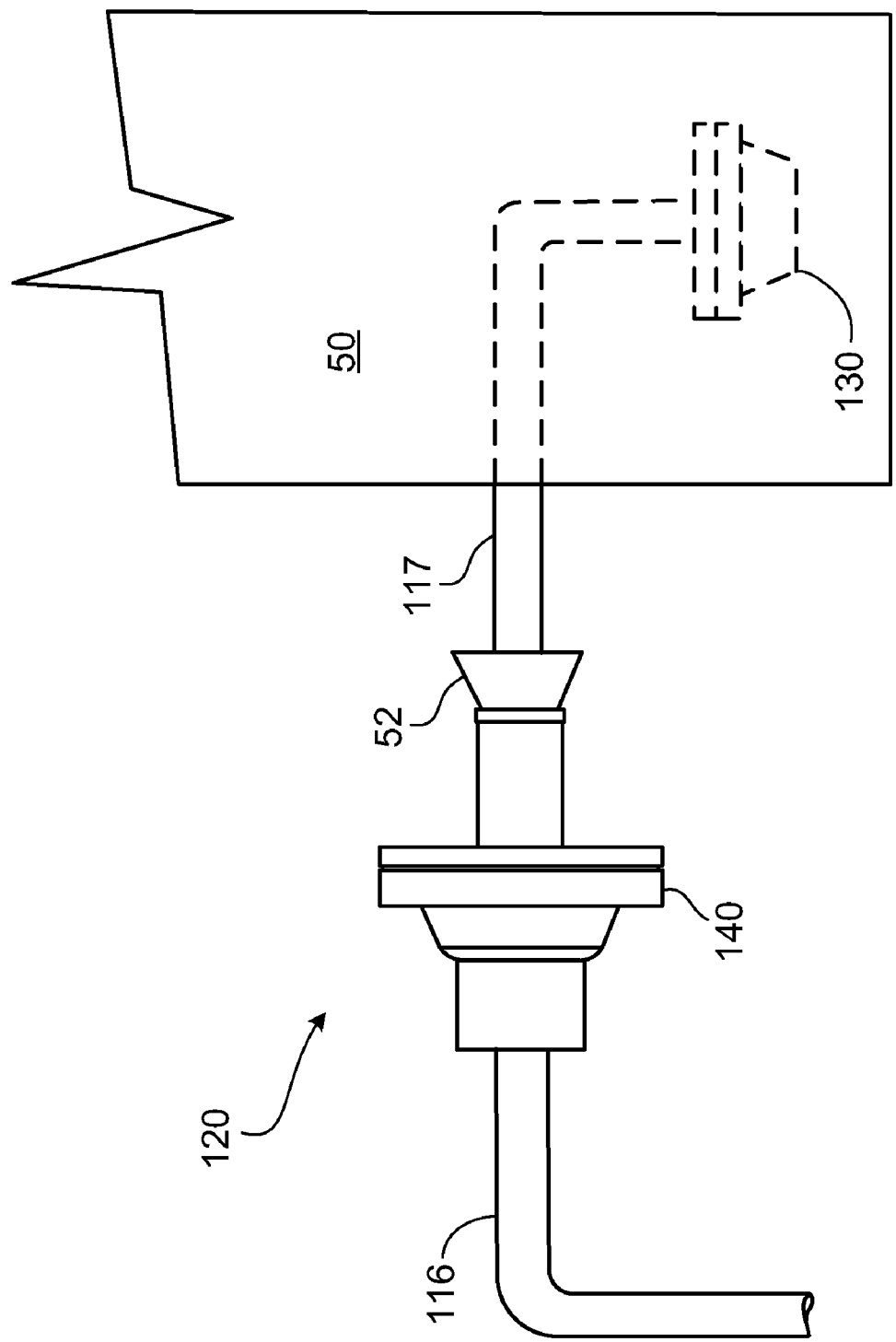
FIG. 2 is schematic view of a pressure sensor assembly.

As shown in FIG. 2, the pressure transducer assembly 120 includes the pressure transducer 130 and the transducer protector 140. Referring to FIGS. 3A and 3B, the transducer protector 140 includes a body 143 that defines a fluid pathway. The body 143 includes a vent assembly compartment 142 in which the micro-porous membrane 144 and the self-sealing vent structure 146 are disposed. A first open end 148 can be connected to the dialysis machine 50, e.g., via a machine fitment 52 (FIG. 2) and tubing 117, and provides for fluid communication between the pressure transducer 130 and the vent assembly compartment 142. A second open end 149 can be connected to the tubing (e.g., connecting tube 116) of the extracorporeal circuit 100 (FIG. 1) to provide for communication between the vent assembly compartment 142 and blood flowing within the circuit 100. This arrangement allows gas (e.g., air) to pass through the vent assembly 141 from the second open end 149 toward the first open end 148, while inhibiting the passage of blood, and thereby allows the pressure transducer 130 to measure changes in air pressure.

The micro-porous membrane 144 allows gas (e.g., air) to pass through the vent assembly compartment 142, but impedes the flow of liquid, thereby inhibiting or preventing the blood from directly contacting, and possible contaminating, the pressure transducer 130 on the opposite side of the vent assembly compartment 142. The micro-porous membrane 144 can also help to inhibit (e.g., prevent) foreign particles and organisms from entering the extracorporeal circuit 100 from the transducer side of the vent assembly compartment 142.

The micro-porous membrane 144 includes a hydrophobic material, such as polytetrafluoroethylene (PTFE) (e.g., expanded polytetraflouroethylene (ePTFE)) backed by a mesh material. In some embodiments, the membrane 144 is a fibrous carrier with a matted and woven layer on top of which ePTFE or other micro-porous material is applied. A suitable membrane has an average pore size of about 0.05 to about 0.45 microns (e.g., about 0.22 microns or about 0.2 microns). Suitable membranes are available from Pall Corporation, East Hills, N.Y., under the Versapor® mark and from W. L. Gore & Associates, Inc., Newark, Del.

The self-sealing vent structure 146 is a solid porous block, having an average pore size of about 15 to about 45 microns, that allows air to pass through the vent assembly compartment 142. In some embodiments, the self-sealing vent structure 146 is formed of a blend of polyethylene (e.g., high density polyethylene (HDPE)) and carboxymethylcellulose (CMC), a blend of polystyrene and methyl-ethyl-cellulose or of polypropylene- or polyethylene-based porous material. Such materials are available from Porex Corporation, Fairburn, Ga., such as EXP-816, which is a product containing 90% by weight polyethylene and 10% by weight carboxymethylcellulose with an average pore size of about 30 microns to about 40 microns. However, other percentages of the materials can be used, as well as other materials and other pore sizes. For example, the vent structure 146 can include about 80% to about 95% by weight high density polyethylene and about 5% to about 20% by weight carboxymethylcellulose.

Figure 4A:
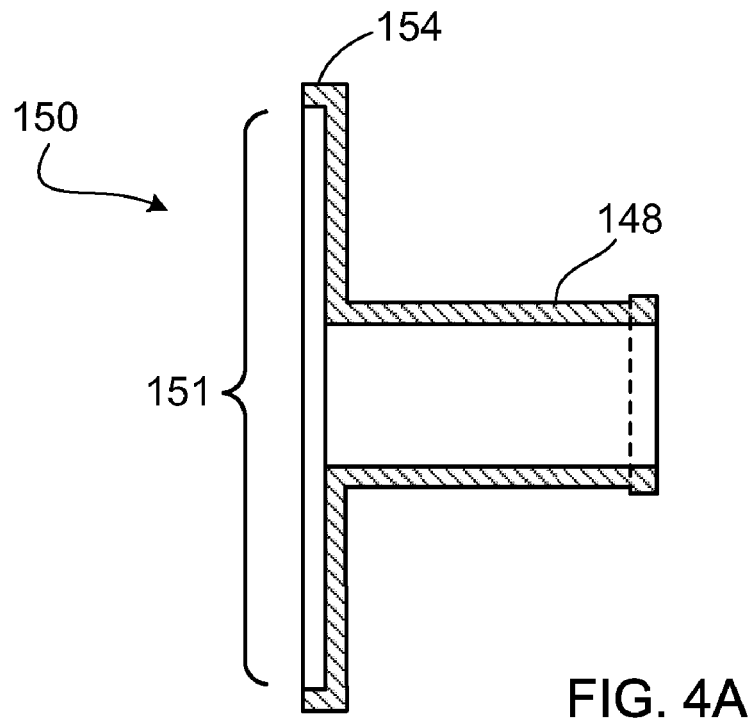
FIG. 4A is a cross-sectional side view of a first part of the transducer protector of FIG. 3A.
Figure 4B:
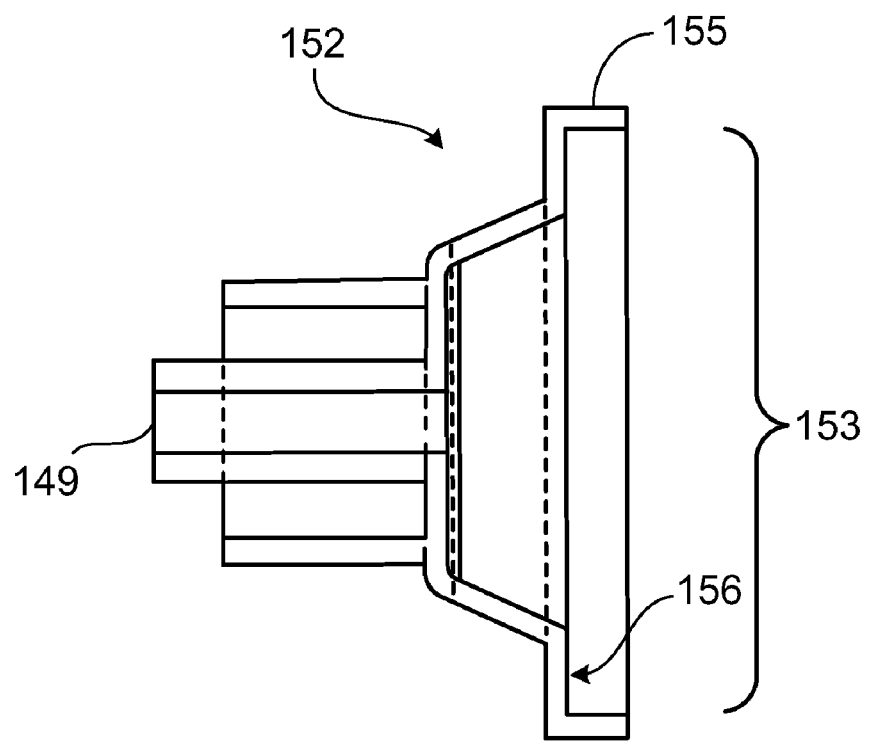
FIG. 4B is a cross-sectional side view of a second part of the transducer protector of FIG. 3A.

Referring to FIGS. 4A and 4B the body 143 of the transducer protector 140 can be formed from two parts. As shown in FIG. 4A, a first part 150 defines the first open end 148 and a first portion 151 of the vent assembly compartment 142. As shown in FIG. 4B, a second part 152 defines the second open end 149 and a second portion 153 of the vent assembly compartment 142. The first and second parts 150, 152 of the transducer protector 140 can be formed of one or more medical grade materials. Plastics, such as polyvinylchloride, polycarbonate, polyolefins, polypropylene, polyethylene or other suitable medical grade plastic can be used because of their ease of manufacturing, ready availability and disposable nature. The first and second parts 150, 152 of the transducer protector can be separately formed, such as by molding (e.g., extruding, blow molding or injection molding).

Figure 5A:
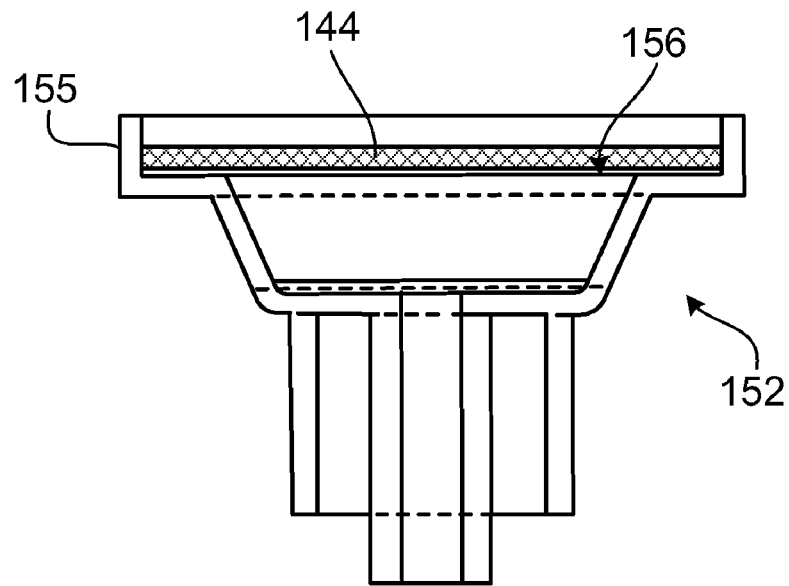
FIGS. 5A-5C are cross-sectional views illustrating the assembly of the transducer protector of FIG. 3A.
Figure 5B:
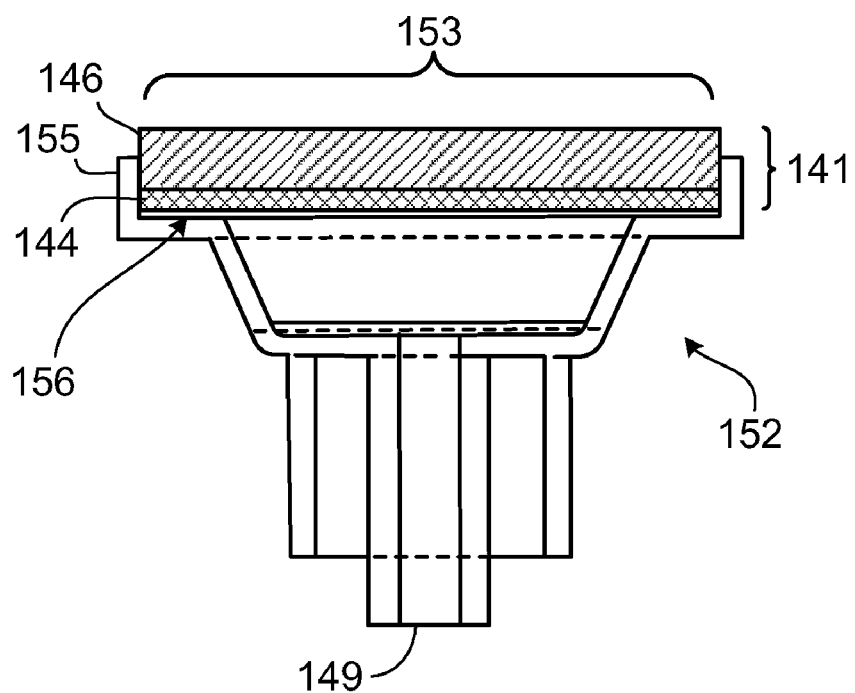
Figure 5C:
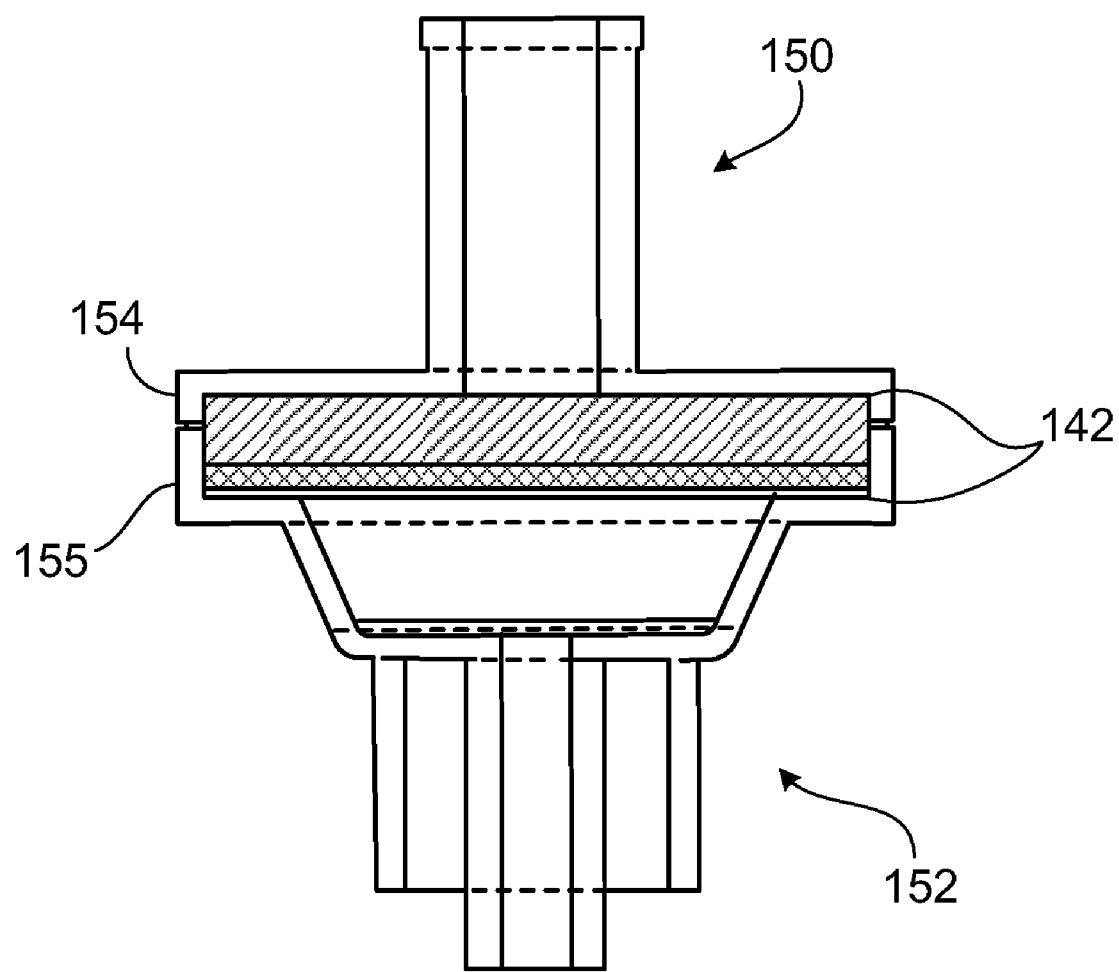

The first and second parts 150, 152 of the transducer protector 140 each include an associated sidewall 154, 155. The sidewalls 154, 155 of the respective first and second parts 150, 152 help to retain the micro-porous membrane 144 and the self-sealing vent structure 146 within the vent assembly compartment 142 following assembly. As illustrated in FIGS. 5A-5C, the transducer protector 140 is assembled by first inserting the micro-porous membrane 144 into the second part 152 in a position in which the micro-porous membrane 144 is disposed within the second portion 153 of the vent assembly compartment 142. In this position, as shown in FIG. 5A, the micro-porous membrane 144 is seated against a ledge 156 that is defined by the second part 152. The micro-porous membrane 144 can be dimensioned such that a press-fit is provided between the micro-porous membrane 144 and the sidewall 155 of the second part 152 of the transducer protector 140. Next, as illustrated in FIG. 5B, the self-sealing vent structure 146 is positioned adjacent the micro-porous membrane 144 in a position in which the self-sealing vent structure 146 is partially disposed within the second portion 153 of the vent assembly compartment 142. The self-sealing vent structure 146 can also be dimensioned such that a press-fit is provided between the vent structure 146 and the sidewall 155 of the second part 152 of the transducer protector 140. Then, as illustrated in FIG. 5C, the first part 150 can be connected to the second part 152 of the transducer protector 140 such that the respective sidewalls 154, 155 of the first and second parts 150, 152 of the transducer protector 140 together define the vent assembly compartment 142. The first and second parts 150, 152 of the transducer protector 140 can be bonded to each other, such as by welding, adhering (e.g., with epoxy), solvent bonding, mating threaded connections or other suitable method.

Referring to FIGS. 6A and 6B, pressure can be read out and displayed through the electronics of the dialysis machine 50. Dynamic pressure pulse variations may take place, and will be transmitted through tubing sections 110, 140 to the pressure transducer 130, for a continuous pressure measurement. The measured pressure pattern is compared to a machine pressure pattern, which is determined as a function of pump operation. If there is a variance between the measured pressure pattern and the machine pressure pattern automatic shut-off can occur and/or an alarm can be sounded. If, for example, the micro-porous membrane 144 ruptures, thereby allowing liquid (e.g., blood) to contact the self-sealing vent structure 146, the vent structure 146 will self seal and inhibit (e.g., prevent) fluid, including gases, from passing. As a result, as illustrated in FIG. 6B, the pressure transducer 130 will sense a change in the pressure pattern (e.g., a diminished pressure pulse), which the associated dialysis machine electronics will interpret as a possible membrane rupture.

Air Release Chamber

Figure 7A:
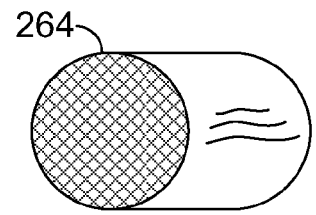
FIG. 7A is a schematic top view of the air release chamber of FIG. 7.
Figure 7:
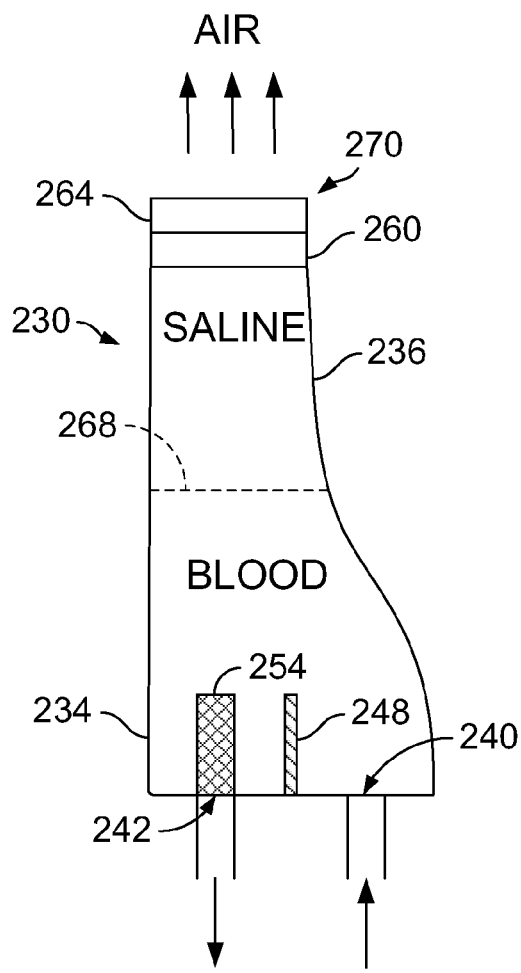
FIG. 7 is a schematic cross-sectional view of an air release chamber with a vent assembly.
Figure 7B:
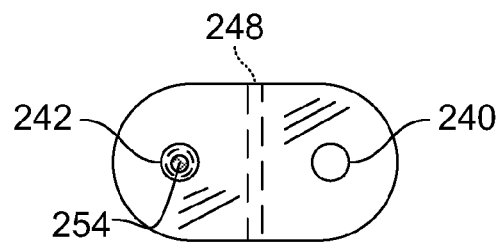
FIG. 7B is a schematic bottom view of the air release chamber of FIG. 7.
Figure 7C:
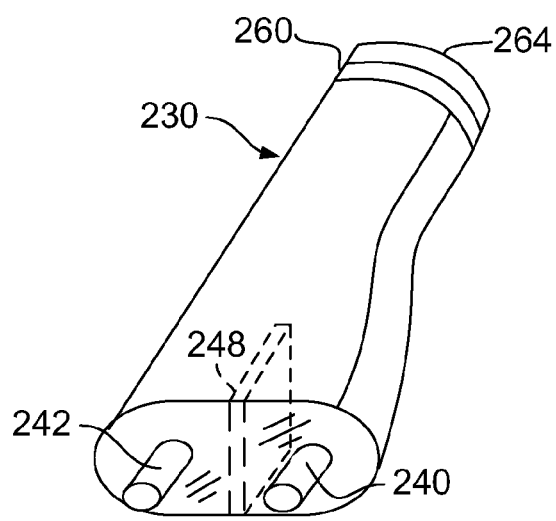
FIG. 7C is a schematic perspective view of the air release chamber of FIG. 7.
Figure 7D:
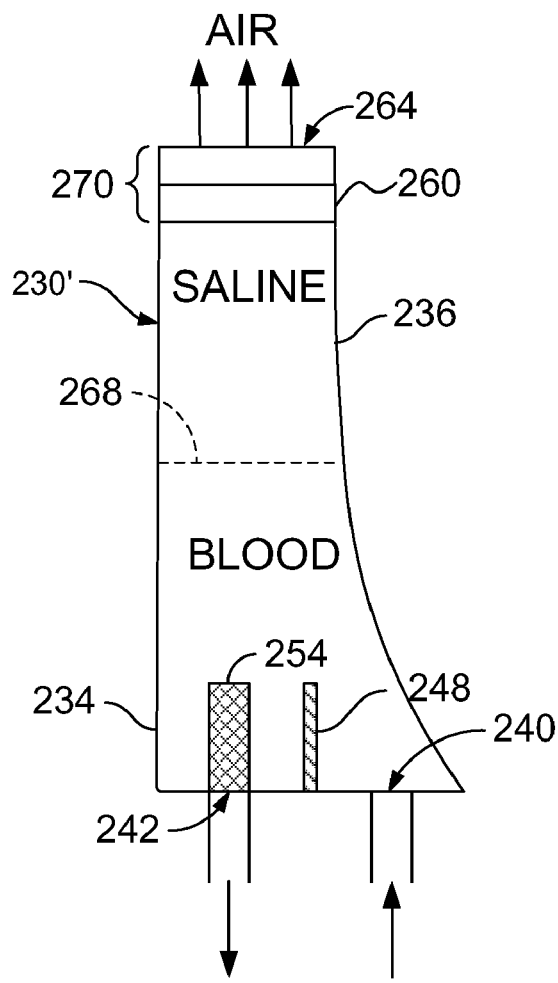
FIGS. 7D, 7E, and 7F are each schematic cross-sectional views of air release chambers.
Figure 7E:
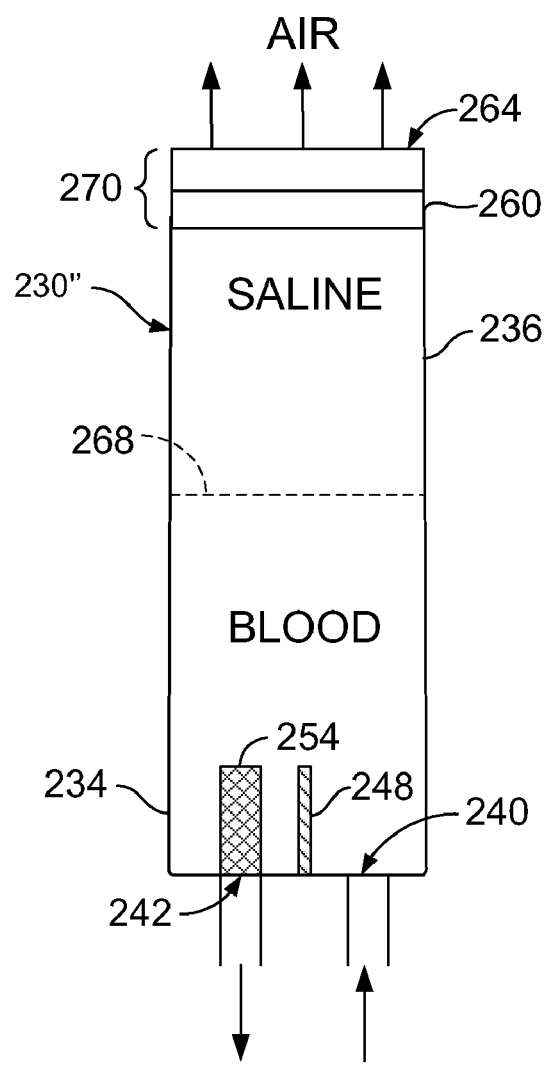
Figure 7F:
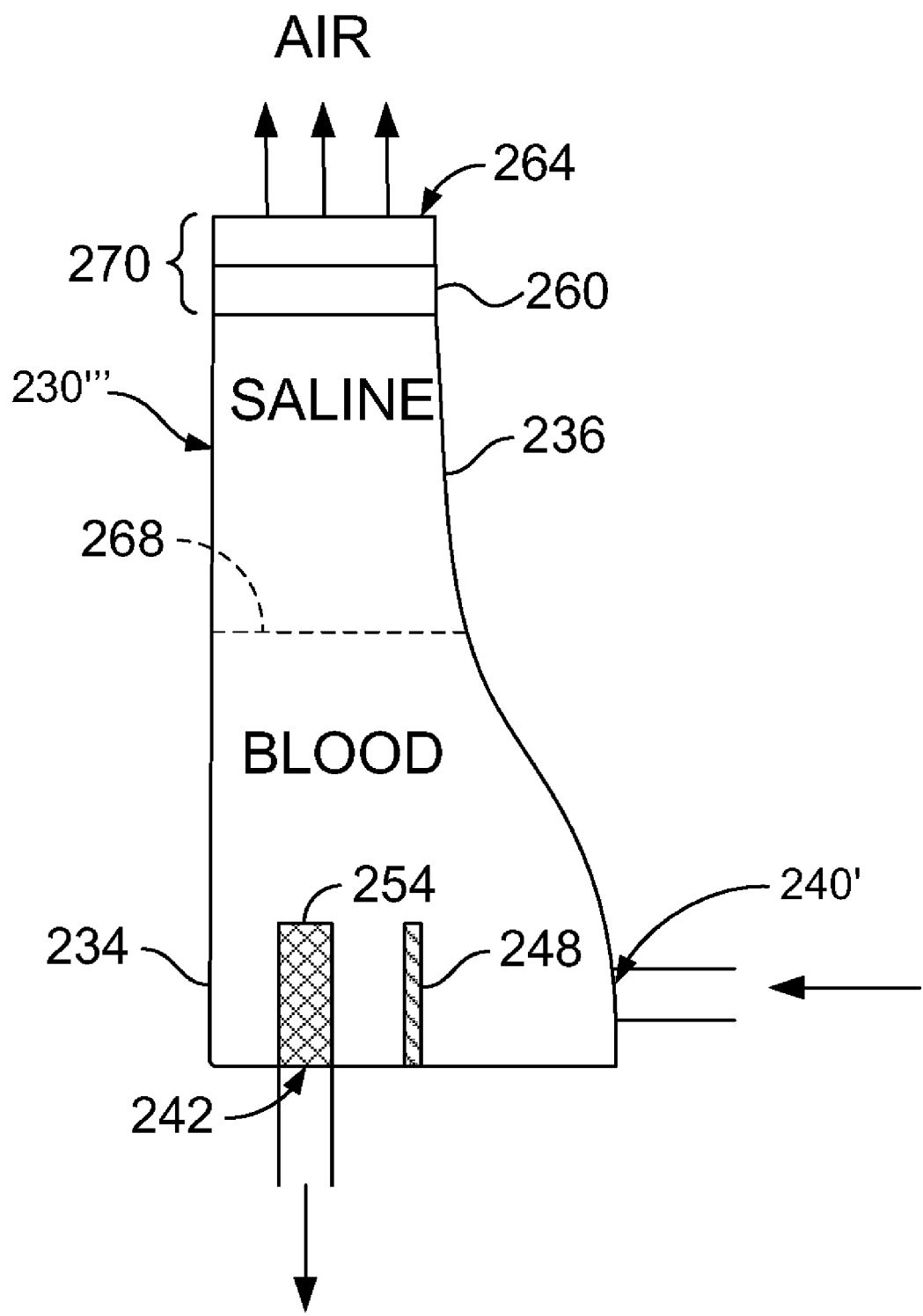

Referring to FIGS. 7, 7A, 7B and 7C, the air release chamber 230 is substantially hollow for filling with a liquid. The chamber 230 can be used for removing gas (e.g., air bubbles) from blood. The chamber 230 has a bottom region 234 and a top region 236, where the bottom and top are relative to the chamber's orientation during use. An entry port 240 and an exit port 242 are in the bottom region 234 of the chamber 230. In some implementations, the ports 240, 242 are located in a bottom surface of the chamber 230. In other implementations, as shown in FIG. 7F, at least one of the ports 240, 242 is located in a side surface of the chamber 230. In some implementations, a dam 248 is between the ports 240, 242. The dam 248 extends at least part way from one side wall to an opposite side wall. In some implementations, the dam 268 contacts each side wall so that all fluid entering entry port 240 flows over the top of the dam 248 before flowing out the exit port 242. In some implementations, a clot filter 254 is positioned adjacent to the exit port 242. Fluid flows through the clot filter 254 prior to flowing out of the exit port 242. In some implementations, the clot filter 245 has a porosity of about 50 microns to about 500 microns.

The ports 240, 242 are holes in the chamber 230 which can be in fluid communication with tubular shaped extensions. The extensions are able to be connected to tubes, such as by pressure fitting or bonding. The extensions can be integrally formed with the chamber 230 or subsequently attached to the chamber 230, such as by bonding or welding.

At the top region 236 of the chamber 230 is a self-sealing vent assembly 270. The self-sealing vent assembly 270 includes a micro-porous membrane 260 and a vent structure 264. The assembly with the vent structure 264 and micro-porous membrane 260 may provide reduced condensation or minimize condensation on the micro-porous membrane 260. The micro-porous membrane 260 allows gas (e.g., from air bubbles in the blood) to vent from the chamber 230. Pores in the micro-porous membrane 260 are small enough to keep foreign particles and organisms from entering the chamber 230 from the outside air.

In some implementations, the membrane 260 includes a hydrophobic material, such polytetrafluoroethylene (PTFE) (e.g., expanded polytetrafluoroethylene (ePTFE)) In some embodiments, the membrane 260 is a fibrous carrier with a matted and woven layer on top of which ePTFE or other micro-porous material is applied. The hydrophobic micro-porous membrane 260 keeps liquid from leaking out of the chamber 230 when the chamber 230 is substantially filled with liquid and allow air to pass through. A suitable membrane has an average pore size of about 0.05 microns to about 0.45 microns (e.g., about 0.22 microns, about 0.2 microns). Suitable membranes are available from Pall Corporation, East Hills, N.Y., under the Versapor® mark and from W. L. Gore & Associates, Inc., Newark, Del.

The vent structure 264 is a solid porous block, having an average pore size of about 15 micron to about 45 microns, that allows air to pass through and escape from the chamber. The vent structure 264 is also a self-sealing vent structure. In some implementations, the vent structure 264 is formed of a blend of polyethylene (e.g., high density polyethylene (HDPE)) and carboxymethylcellulose (CMC), a blend of polystyrene and methyl-ethyl-cellulose or of polypropylene- or polyethylene-based porous material. Such materials are available from Porex Corporation, Fairburn, Ga., such as EXP-816, which is a product containing 90% by weight polyethylene and 10% by weight carboxymethylcellulose with an average pore size of about 30 microns to about 40 microns. However, other percentages of the materials can be used, as well as other materials and other pore sizes. For example, the vent structure 264 can include about 80% to about 95% by weight high density polyethylene and about 5% to about 20% by weight carboxymethylcellulose.

When the vent structure 264 comes into contact with liquid, e.g., humidity or moisture, the swelling agent (e.g., cellulose component, e.g., carboxymethylcellulose) of the vent structure expands, thereby closing off the pores in the polymer component (e.g., high density polyethylene) of the vent structure 264. The vent structure 264 is mounted adjacent to and just above the membrane 260 so that the hydrophobic membrane 260 is located between the vent structure 264 and the chamber 230. The vent structure 264 inhibits (e.g., prevents) condensation from accumulating on and contacting the membrane 260. In some embodiments, the vent structure 264 directly contacts the membrane 260. The vent structure 264 can be substantially disc shaped or can be another shape that is compatible with a chamber on which the vent structure 264 is mounted. In embodiments, the vent structure 264 is about 0.1 mm to about 10 mm thick.

When the chamber 230 is filled with blood, inhibiting (e.g., preventing) the protein in the blood from accumulating on the membrane 260 can maintain the hydrophobic characteristic of the membrane 260. Whole blood can be kept from the membrane 260 by providing a barrier between the blood and the membrane 260, such as a liquid barrier 268, as described further below. The height of the chamber 230 is sufficient to maintain this barrier 268 and inhibits (e.g., prevents) the liquid above the barrier 268 from substantially mixing with liquid below the barrier 268.

The shape of the chamber is approximately elongate. In some implementations, such as those shown in FIGS. 7 and 7D, the bottom region 234 of the chamber 230, 230' is wider than the top region 236, such that the chamber 230, 230' has a quasi-conical shape or a flare at the bottom. In some implementations, such as those shown in FIG. 7E, the top and bottom dimensions of the chamber 230" are approximately equal so that the chamber 230" has a rectangular or cylindrical shape. The bottom region 234 can also be narrower than the top region 236. If the ports 240, 242 are in the bottom surface of the chamber, the bottom surface has a sufficiently large dimension to accommodate the ports 240, 242 as well as any tubes coupled to the ports for directing fluid into and out of the chamber. For example, if the tubing has an outer diameter of 6.25 mm, the bottom surface is at least 12.5 mm wide. The chamber 230 is sized to maintain the liquid barrier 268. In some implementations, the chamber 230 is at least about two inches in height, (e.g., about three to about four inches).

The chamber is formed of a material suitable for medical devices, that is, a medical grade material. Plastics, such as polyvinylchloride, polycarbonate, polyolefins, polypropylene, polyethylene or other suitable medical grade plastic can be used because of their ease of manufacturing, ready availability and disposable nature. The chamber is formed, such as by molding, for example, extruding, blow molding or injection molding. The chamber can be formed of a transparent or clear material so that the liquid flowing through the chamber can be observed.

Figure 8:
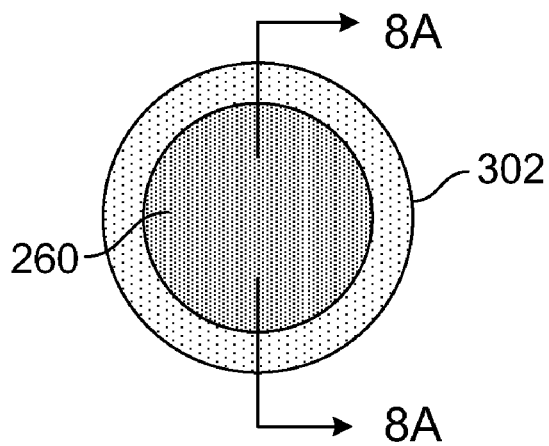
FIG. 8 is a schematic top view of a hydrophobic filter assembly.
Figure 8A:
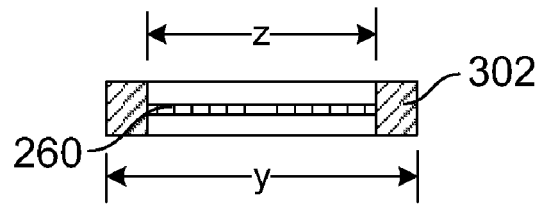
FIG. 8A is a schematic cross-sectional view of the hydrophobic filter assembly of FIG. 8, taken along line 8A-8A.
Figure 9:
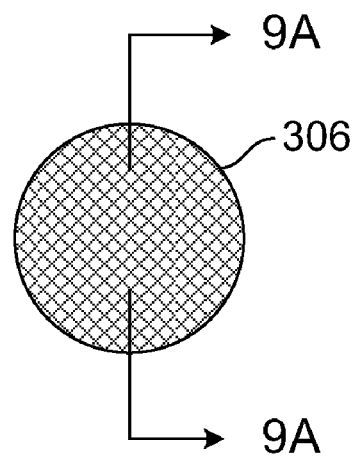
FIG. 9 is a schematic top view of a vent structure.
Figure 9A:
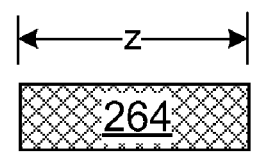
FIG. 9A is a cross-sectional view of the vent structure of FIG. 9, taken along line 9A.

The construction of the vent assembly 270 is described with respect to the following figures. Referring to FIGS. 8 and 8A, a ring 302 holds the micro-porous membrane 260 within its inner diameter. The ring can be formed of plastic, such as one of the plastics described herein. The micro-porous membrane 260 can be insert-molded into the ring 302. That is, the micro-porous membrane 260 can be placed into a mold and held in place. The plastic for the ring 302, which can be polyethylene, polystyrene or another other suitable material, is then injected into a mold to form the ring 302. The ring 302 has an inner diameter z and an outer diameter y. Referring to FIGS. 9 and 9A, the vent structure 264 has a diameter of z.

Figure 10:
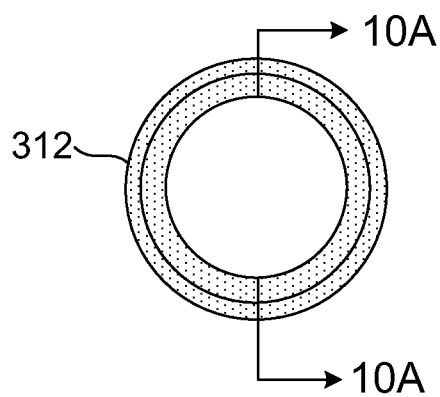
FIG. 10 is a schematic top view of an insert.
Figure 10A:
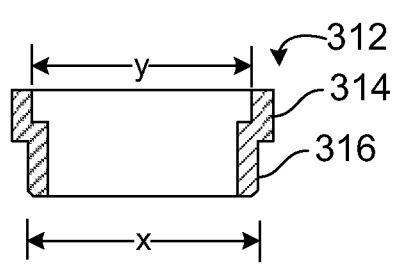
FIG. 10A is a cross-sectional view of the insert of FIG. 10, taken along line 10A-10A.
Figure 10B:
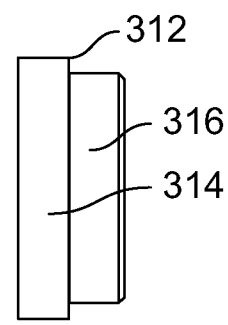
FIG. 10B is a side view of the insert of FIG. 10.

Referring to FIGS. 10 and 10A, an insert 312 is configured to hold the ring 302 and the vent structure 264. The insert 312 has a first portion 314 and a second portion 316. The first portion 314 has a greater outer diameter and greater inner diameter than the outer diameter and inner diameter of the second portion 316. In some embodiments, the inner diameter of the first portion 314 is y and the outer diameter of the second portion 316 is x. The transition between the first portion 314 and the second portion 316 forms a ledge. The insert 312 can be formed of the same plastic or a different material from the plastic ring.

Figure 11:
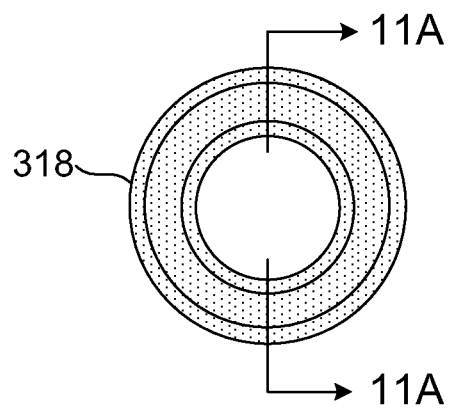
FIG. 11 is a schematic top view of a retainer.
Figure 11A:
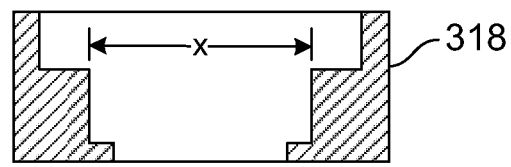
FIG. 11A is a cross-sectional view of the retainer of FIG. 11, taken along line 11A-11A.

Referring to FIGS. 11 and 11A, a retainer 318 is configured to hold the ring 302, the vent structure 264 and the insert 312. In some embodiments, the retainer 318 has a constant outer diameter, that is, the outer diameter does not change from one end of the retainer 318 to the other. In some embodiments, the retainer 318 has three unique inner diameters. Near the top (as shown in the figure) of the retainer 318, the inner diameter is the greatest and in some embodiments, the inner diameter is equal to or just slightly greater than the outer diameter of the first portion 314 of the insert 312. Near the bottom of the retainer 318, the retainer 318 can have an inner diameter that is less than z, or less than the diameter of the vent structure 264. Between the bottom and the top of the retainer 318, the inner diameter can be about equal to x, that is, about equal to or slightly greater than the outer diameter of the second portion 316 of insert 312.

Referring to FIG. 12, an assembly 300 can be formed from the ring 302, vent structure 264, insert 312 and retainer 318. The retainer 318 holds the vent structure 264 so that the portion of the retainer with an the inner diameter that is less than the vent structure's diameter inhibits (e.g., prevents) the vent structure 306 from escaping. The ring 302 is within the inner diameter of the retainer 318 and adjacent to the vent structure 264. In some embodiments, the ring 302 has sufficient height that the vent structure 264 can be seated within the inner diameter of the ring 302. The first portion 314 of the insert 312 fits between the outer diameter of the ring 302 and the inner diameter of the retainer 318. The retainer 318 can be bonded to the insert 312, such as by welding, adhering, solvent-bonding or other suitable method. The second portion 316 of the insert 312 forms a shank that is sized to fit into a chamber, as described further herein.

Figure 15:
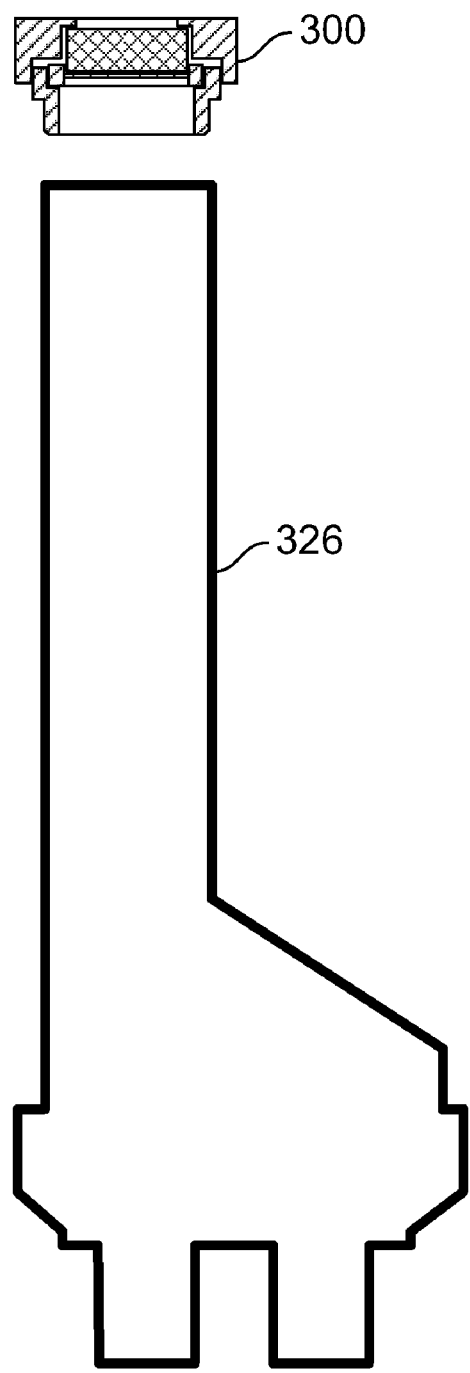
FIG. 15 is a schematic cross-sectional view of a bottom entry/bottom exit chamber and a vent assembly.
Figure 16:
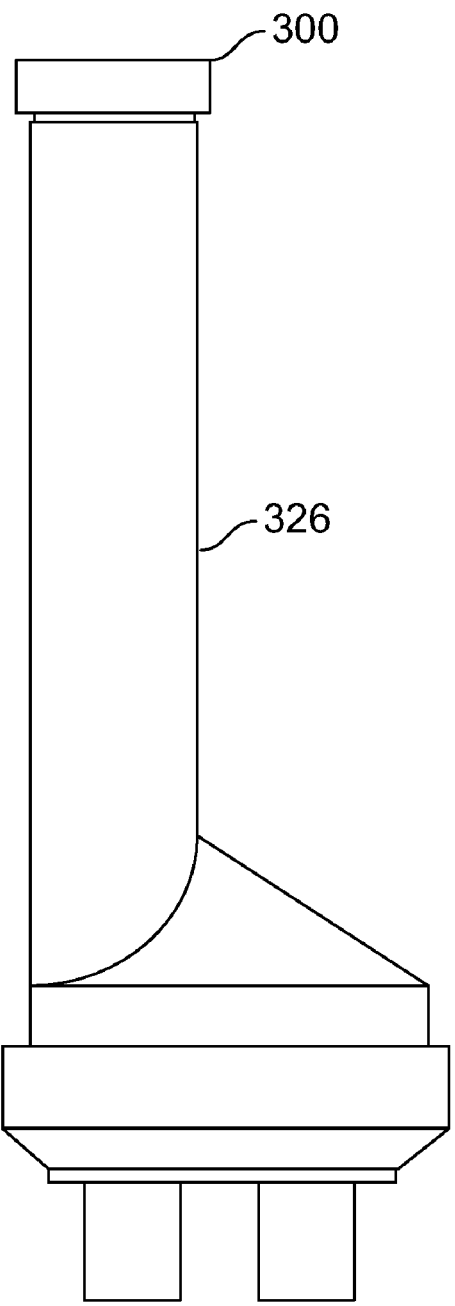
FIG. 16 is a schematic side view of a bottom entry/bottom exit chamber with a vent assembly.

Referring to FIG. 13, the chamber can be formed from two parts. A two port cap 322 can form a bottom of the chamber. A gravity chamber 324 can form the top of the chamber. Referring to FIG. 14, when the cap 322 and gravity chamber 324 are brought together, they form a chamber body 326. The top of the chamber body 326 is sized so that the shank of the assembly 300 can be fit into the chamber body 326, as shown in FIGS. 15 and 16. The chamber body 326 and the assembly 300 can be sealed together, such as by welding, adhering, solvent-bonding or other suitable method.

Figure 20:
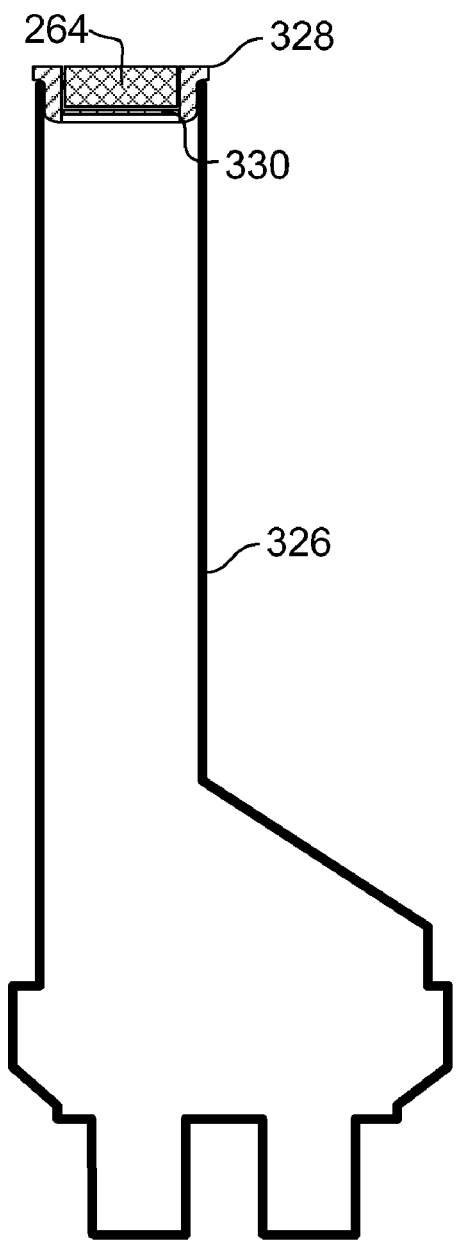
FIG. 20 is a schematic cross-sectional view of a bottom entry/bottom exit chamber and a vent assembly.
Figure 21:
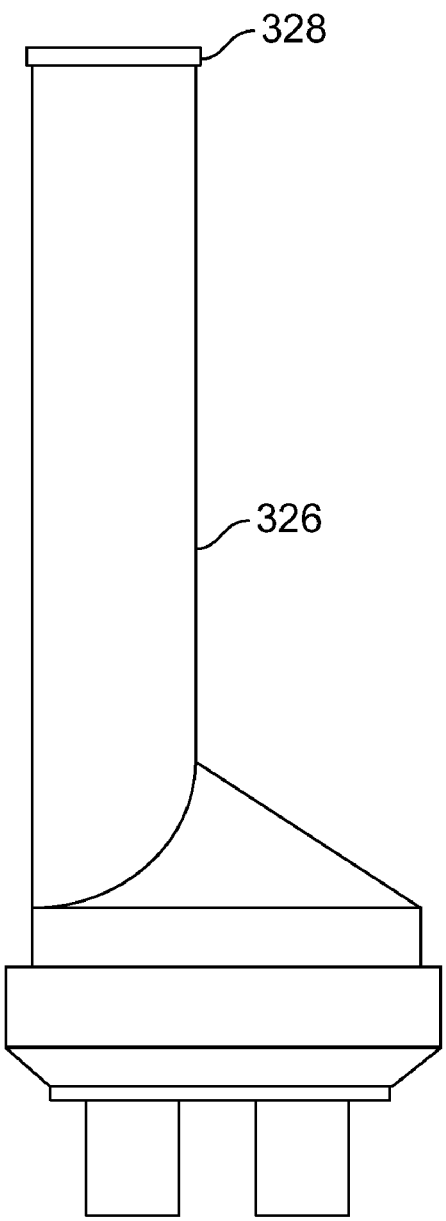
FIG. 21 is a schematic side view of a bottom entry/bottom exit chamber and a vent assembly.

In other implementations, a different type of assembly can be formed. Referring to FIGS. 17, 17A and 17B, for example, a support 328 can have an inner diameter in which the micro-porous membrane 260 is held. The inner diameter of the support 328 can be x. The support 328 can have a flange that extends outwardly from the outer diameter at a top of the support 328. As shown in FIG. 18, the vent structure 264 can fit within the support 328 and on the micro-porous membrane 260. The micro-porous membrane 264 can be insert-molded into the support 328. The vent structure 264 can be press-fit into the support 328. Referring to FIGS. 19, 20 and 21, the support 328 is sized so that the support 328 fits into a chamber body 326 with the flange extending beyond the inner diameter of the chamber body 326 to inhibit (e.g., (prevent) the support 328 from being pressed in or falling into the chamber body 326.

Although the vent assemblies described herein are shown as cylindrical, the assembly can have other shapes as well, such as rectangular, polygon, triangular or other suitable cross sectional shapes. Also, the vent assembly can have a threaded portion so that the assembly can be, for example, screwed into the air release chamber. Alternatively, the vent assembly can be welded, adhered with epoxy or otherwise fastened to the top of the chamber.

Methods of Operation

Figure 22:
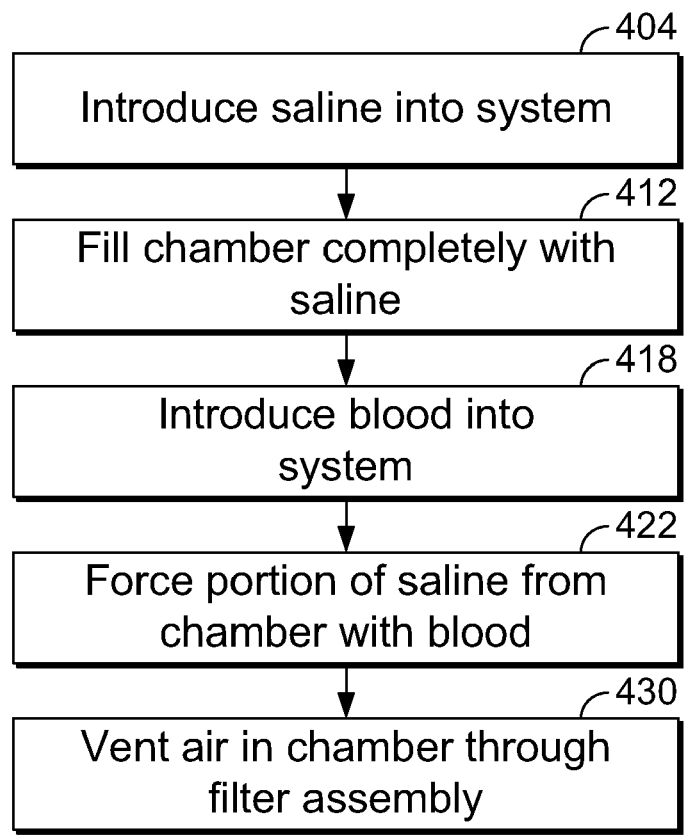
FIG. 22 is a flow diagram for using an air release chamber in an extracorporeal circuit.

Referring to FIGS. 1 and 22, the air release chamber 230 is in line in the extracorporeal fluid circuit of a system for fluid filtration and air removal. A first liquid that is compatible with the liquid to be filtered (the second liquid) is introduced into the system to prime the system (step 404). In hemodialysis, the first liquid is a blood compatible solution, such as saline. The saline flows through the arterial tubing 110 to the arterial pressure sensor assembly 120 so that the pressure of the liquid flowing through the circuit 100 on the arterial side can be monitored, as described above. The saline then flows through a portion of the channel that abuts the pump 160. The pump 160 forces the saline through the circuit 100. The saline then flows to the dialyzer 170. Next, the saline, or the first liquid, flows through the entry port 242 of the chamber 230 and fills the chamber (step 412). To fill the chamber completely, venous line 190 can be clamped to create a positive pressure once the saline is introduced into the chamber 230. Air is forced out the top of the chamber 230 and through the micro-porous membrane 260 and vent structure 264 as saline fills the chamber 230. The saline contacts the membrane 260 and the chamber 230 is substantially free of air once the chamber 230 is completely filled. However, the saline does not exit through the membrane 260, because the membrane 260 is hydrophobic. After the venous line 190 is unclamped, the saline exits through the exit port of the chamber and out the venous line 190.

Figure 23:
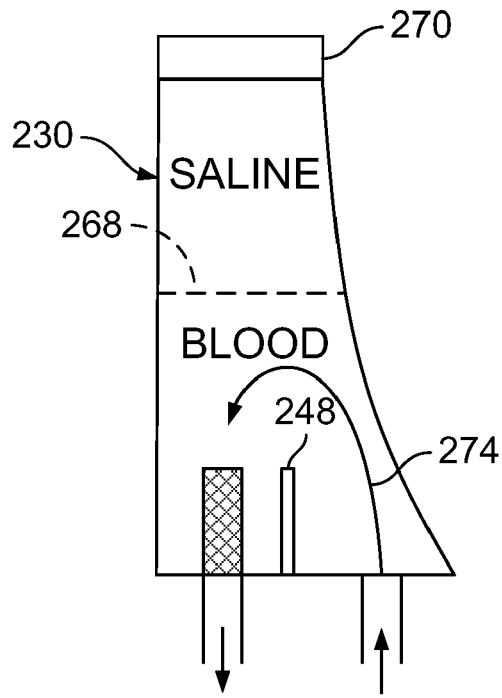
FIG. 23 is a schematic diagram of the blood flow path through an air release chamber.

The second liquid, such as a bodily fluid, for example, blood, is then introduced into the system (step 418). The blood follows the same route as the saline and, for the most part, pushes the saline through the circuit 100. When the blood enters the chamber 230, the blood forces the saline at the bottom of the chamber 230 through the exit port (step 422). However, the blood does not displace all of the saline within the chamber 230. Because of the height of the chamber 230, the blood enters the chamber 230 and only traverses part of the height of the chamber 230 before flowing back down along flow path 274 to the exit port (as shown in the air release chamber formed of transparent material in FIG. 23). An interface 268 between the saline and the blood delineates the furthest extent of most of the blood within the chamber 230. The interface 268 between the blood and saline can visually be observed and stretches across the entire width of the chamber. Because blood and saline are not immiscible, there is some amount of mixing between the two fluids around the interface 268.

The saline keeps the blood from contacting the filter 260. However, a percentage of blood can be present in the saline without hindering the operation of the circuit 100. That is, the saline need not be completely free from blood for the air release chamber 230 to both allow gas (e.g., from air bubbles in the blood) to vent from the circuit 100 and retain the liquid in the circuit 100. The solution that is mostly saline substantially protects the membrane 260 from becoming coated with protein. If the chamber 230 is sufficiently elongated, the blood does not mix with the saline at the top portion of the chamber 230 because the saline remains relatively stagnant as the blood flows through the chamber 230.

Any unbound gas, or air, that is in the blood, such as air that is introduced by the dialyzer 170 or air that comes out of solution from the blood, rises as tiny air bubbles within the blood and saline until the air eventually vents out through the vent assembly 270, including the micro-porous filter 260 and the vent structure (step 430). With a dam 248 inside of the chamber 230, the blood travels up and over the dam 248 rather than straight across the bottom of the chamber 230 out the exit port 242. By directing the flow of blood upwards, the blood with air is not able to flow in and directly back out of the chamber 230 without flowing upwards to at least a height greater then the height of the dam 248. The surface area of the dam 248 and the inner walls of the chamber 230 enables air, including microbubbles, to separate from the blood and exit the circuit 100 through the micro-porous membrane 260.

Throughout the circuit, the blood flows without there being a substantial air-blood interface. Although the blood does not come into contact with air and thus clotting is less likely to occur, the blood can pass through an optional filter in the chamber. In some implementations, after exiting the chamber, the blood passes by or through one or more sensors, such as temperature or air detecting sensors.

Other Embodiments

While certain embodiments have been described above, other embodiments are possible.

Figure 24:
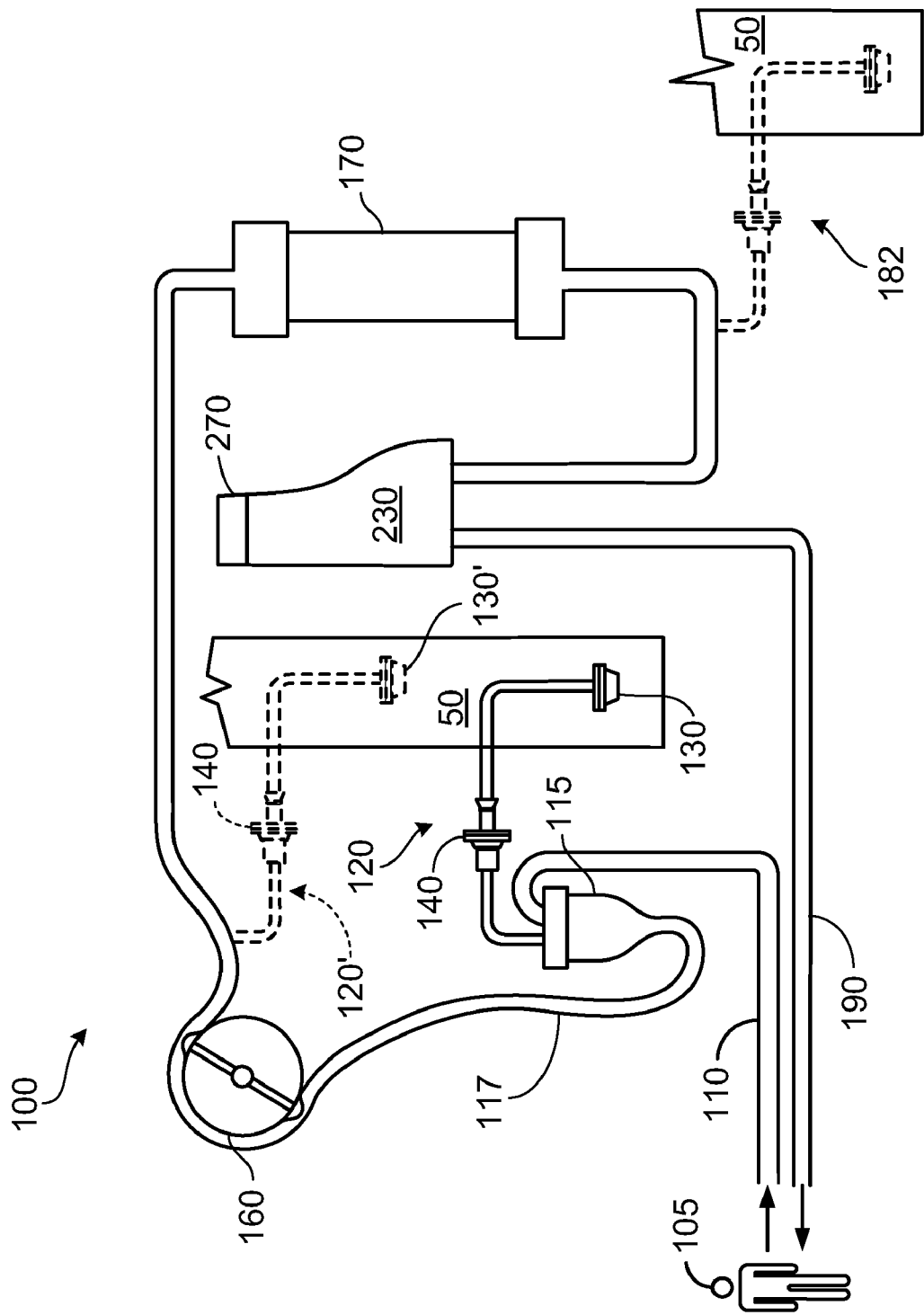
FIG. 24 is a schematic diagram of an extracorporeal circuit for a hemodialysis system including pre-pump and post-pump arterial pressure sensor assemblies and a venous pressure sensor assembly.

As an example, although an embodiment of a extracorporeal circuit has been described in which an arterial pressure sensor assembly is arranged to measure a pre-pump arterial pressure, in some embodiments, as illustrated in FIG. 24, an arterial pressure assembly 120' can, alternatively or additionally, be positioned downstream of the pump 160 for post pump arterial pressure measurement. In some embodiments, the circuit 100 can also include a venous pressure sensor assembly 182 in communication with the venous tubing 180, for monitoring the pressure of liquid (e.g., blood) flowing through the circuit 100 on the venous side. The venous pressure sensor assembly 182 can have the same construction as the arterial pressure sensor assembly 120 described above with regard to FIGS. 3A-5C.

Figure 25:
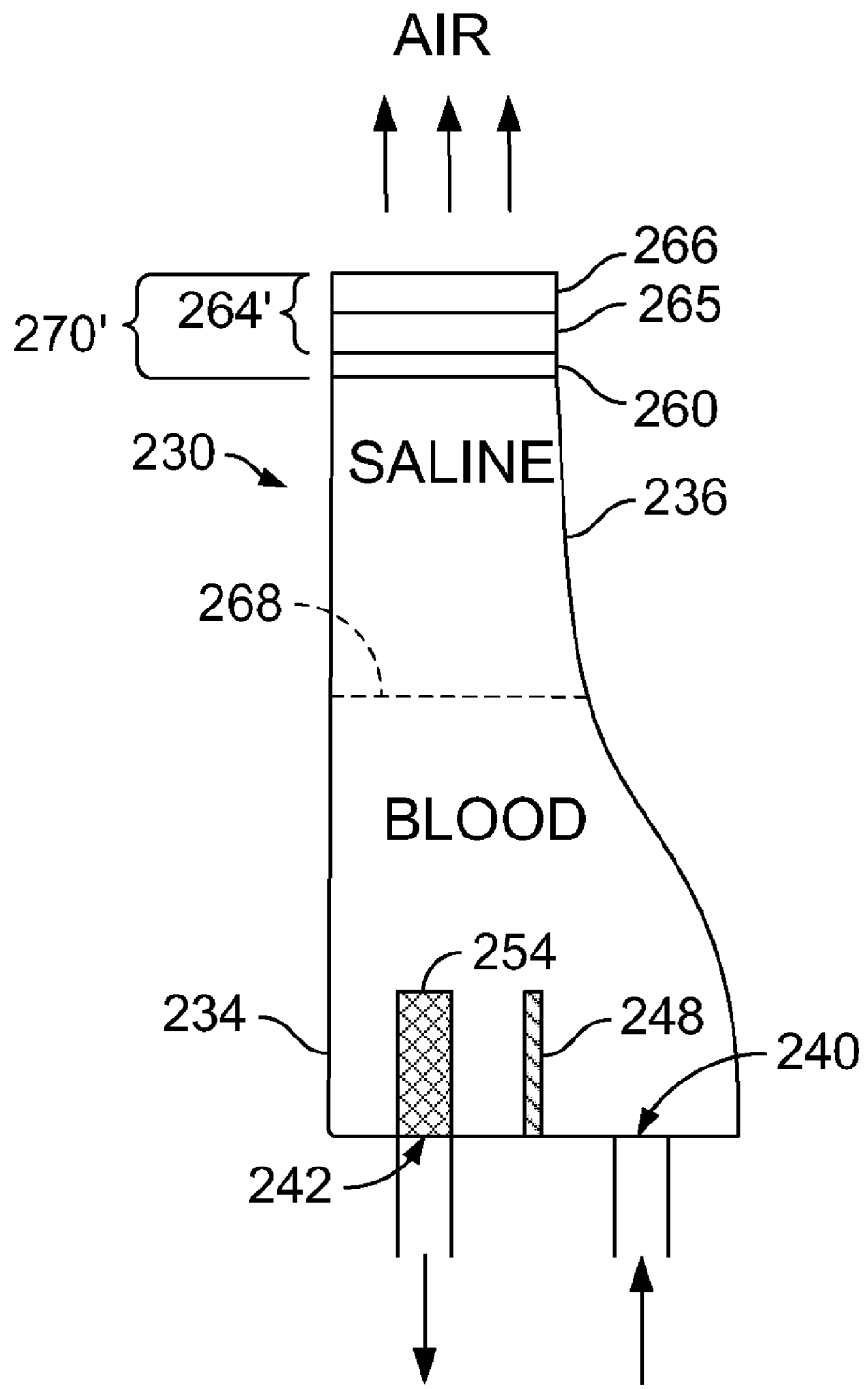
FIG. 25 is a schematic cross-sectional view of an air release chamber with a vent assembly having a multilayer vent structure.

In some implementations, the vent assembly can include a multilayer self-sealing vent structure, where different layers of the vent structure have differing self-sealing (e.g., swelling) characteristics. For example, FIG. 25 shows (in cross-section) a vent assembly 270' including a multilayer self-sealing vent structure 264'. The multilayer self-sealing vent structure 264' includes a first porous layer 265 disposed adjacent the micro-porous membrane 260, and a second porous layer 266 disposed adjacent to the first porous layer 265. The first porous layer 265 is a solid porous block, having an average pore size of about 5 microns to about 45 microns, e.g., about 10 microns. In some embodiments, the first porous layer 265 can be formed of polyethylene (e.g., high density polyethylene (HDPE)), polystyrene, or of polypropylene- or polyethylene-based porous material. Such materials are available from Porex Corporation, Fairburn, Ga. The first porous layer 265 is about 3 mm to about 5 mm thick, e.g., about 4 mm thick. In some embodiments, the first porous layer 265 can be self-sealing. In some embodiments, for example, the first porous layer 265 may include a relatively small amount of carboxymethylcellulose, e.g., about 0% to about 10% by weight carboxymethylcellulose.

The second porous layer 266 is a solid porous block, having an average pore size of about 15 to about 45 microns, e.g., about 30 microns. The second porous layer 266 is about 3 mm to about 5 mm thick, e.g., about 0.4 mm thick. The second porous layer 266 is self-sealing, and is relatively more responsive to the presence of moisture that the first porous layer 265; i.e., the second porous layer 266 has a greater propensity to self-seal (e.g., swell) in the presence of moisture than the first porous layer 265. In some embodiments, the second porous layer 266 is formed of a blend of polyethylene (e.g., high density polyethylene (HDPE)) and carboxymethylcellulose (CMC), a blend of polystyrene and methyl-ethyl-cellulose or of polypropylene- or polyethylene-based porous material. Such materials are available from Porex Corporation, Fairburn, Ga., such as EXP-816, which is a product containing 90% by weight polyethylene and 10% by weight carboxymethylcellulose with an average pore size of about 30 microns to about 40 microns. However, other percentages of the materials can be used, as well as other materials and other pore sizes.

During use, condensation can, for example, form within the vent assembly. The first porous layer 265 allows for a small amount of condensation to be compensated for without activation of the self-sealing property of the second porous layer 266. The first porous layer 265, being relatively less responsive to the presence of moisture (i.e., as compared to the second porous layer 266) slows the progression of moisture from within the chamber 230 toward the second porous layer 266. The first porous layer 265 provides additional surface area (e.g., within pores) where condensation can be pulled out of the air exiting the vent assembly 270' before it reaches self-sealing, second porous layer 266. Thus, small amounts of humidity and moisture (e.g., condensation) from within the air release chamber 230 can be compensated for without triggering closure of the self-sealing vent.

In some embodiments, the air release chamber and one or more other components can be incorporated into an integrated fluid circuit. The integrated fluid circuit has the components described above, such as the air release chamber, formed together in one assembly or integrated molding rather than discrete separate or modular devices. The integrated fluid circuit is adapted to removably seat into a machine, such as a blood purification machine, like a hemodialysis machine The integrated fluid circuit is similar to a cassette or cartridge, where an operator merely snaps the integrated fluid circuit into the machine and after just a few additional connections, begins operation.

Figure 26:
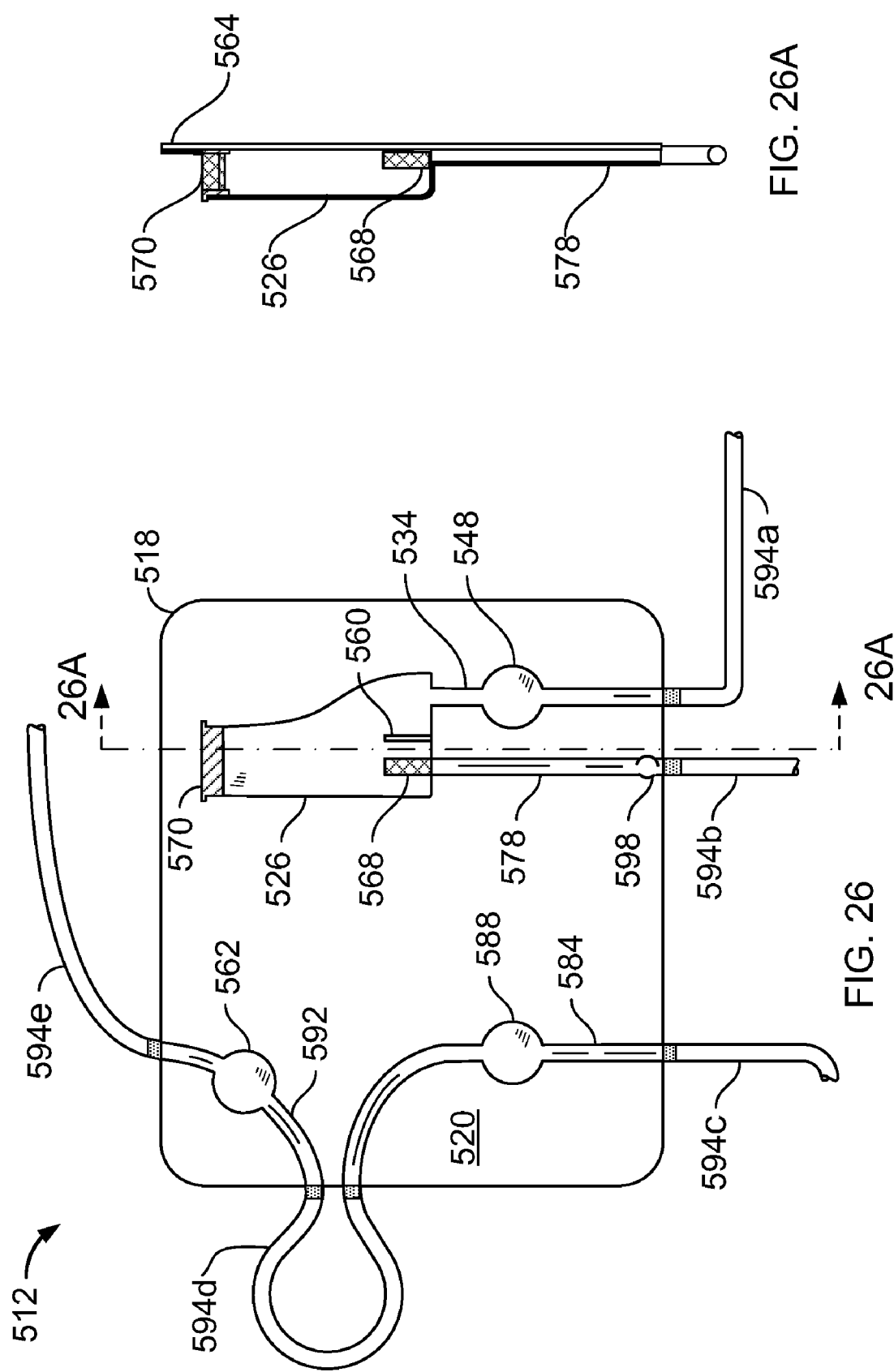
FIG. 26 is a plan view of an integrated extracorporeal circuit.

Referring to FIG. 26, the integrated fluid circuit 512 has a rigid body 518 and a flexible backing (not shown). The rigid body has a substantially flat surface 520 with one or more concave (when viewed from the backside) portions or recessed portions protruding from a front surface of the body 518. The flexible backing can be applied so that the backing covers only the recessed portions or so that the backing covers more than just the recessed portions, up to all of the back surface of the rigid body.

The integrated fluid circuit has a recessed portion that serves as the air release chamber 526. As with the chamber described above, the air release chamber 526 includes a self-sealing vent assembly 570 at a top region and optionally includes a dam 560 and a clot filter 568. The vent assembly 570 can be formed separately from the body 518 and fit into the top of the air release chamber 526, similar to the method described with respect to forming the devices shown in FIGS. 16 and 21. Alternatively, a micro-porous membrane and vent structure can be fit into the integrated fluid circuit after the body 518 has been formed, without a support or retainer.

A first channel 534 in rigid body 518 leads from an edge of the rigid body 518 to a bottom region of the air release chamber 526. Over one portion of the channel 534, a venous recess or pocket 548 is formed. The flexible backing backs the venous pocket 548. The venous pocket 548 is sized so that a transducer in the machine can measure the venous fluid pressure through the flexible backing. A second channel 578 extends from the outlet of the air release chamber 526 to an edge of the rigid body 518. The first and second channels extend to the same or different edges of the rigid body 518. The first channel 534 and second channel 578 are in fluid communication with the air release chamber 526.

In some implementations, a third channel 584 is formed in the rigid body 518. The third channel 584 is not in fluid communication with the first or second channels when the integrated fluid circuit is not in the machine or connected to a dialyzer. In some implementations, an arterial pocket 588 is formed along the third channel 584. The arterial fluid pressure can be measured through the flexible backing of the arterial pocket 588. One end of the third channel 584 extends to one edge of the rigid body 518 and the other end extends to the same or a different edge, as shown in FIG. 26.

Optionally, a fourth channel 592 extends across the rigid body 518. A post-pump arterial pocket 562 overlaps the fourth channel 592. In some implementations, additional recesses and channels are formed in the rigid body.

In some implementations, tubes 594a, 594b, 594c, 594d and 594e are connected to the rigid body 518, such as at the locations where the first, second, third and fourth channels extend to the edges. The tubes are connected to the rigid body using techniques known in the art. In some embodiments, the tubes fit into a pre-formed grooves in the rigid body 518. The tubes can be pressure fitted into the grooves. In other implementations, the tubes are clipped onto the rigid body 518. Optionally, at the end of the tubes 594a, 594b, 594c and 594e are fasteners for connecting the tubes to components of the machine, such as the dialyzer or to a patient. Tube 594d wraps around a peristaltic pump in the machine Tubes 594a and 594e connect to a dialyzer. Tubes 594b and 594c connect to a patient.

Each of the recesses can protrude from the flat surface 520 to approximately the same distance. Alternatively, some of the recesses, such as the channels, may be shallower than other recesses, such as the air release chamber 526. Referring to FIG. 26A, a cross section of the integrated circuit 512 shows an outline of the part of chamber 526, the clot filter 568, the side of second channel 578, the membrane 564 and a cross section of the vent assembly 570. The rigid body 520 can have an overall thickness of less than about 2 mm, such as less than about 1 mm. Flexible membrane 564 covers the back of the rigid body 520.

In some implementations, instead of one or more of the channels being formed in the rigid body 518, a tube is connected directly to a feature in the rigid body. For example, instead of forming second channel 578, tube 594b can be connected directly to the air release chamber 526.

In some implementations, the integrated circuit 512 has two rigid sides. The first rigid side is as described above. The second rigid side is substantially flat with openings located adjacent to the pockets formed in the first side. The openings are covered with a flexible membrane.

In some implementations, the integrated circuit 512 has posts that extend from one or more sides of the circuit. The posts can mate with recesses in the machine, ensuring correct registration of the integrated circuit 512 with components, such as sensors, in the machine. In some implementations, the integrated circuit 512 has latches, clips or other such device for registering the integrated circuit 512 with the machine and locking the integrated circuit 512 in place.

The machine can have a mechanism that holds the integrated circuit in place. The mechanism can include a door, a locking device or a suction device for holding the integrated circuit in tight contact with the machine. When the integrated circuit is seated in the machine, pressure transducers interface with the flexible backing to directly measure the fluid pressure at each of the corresponding locations. Holding the integrated circuit in contact with the machine allows the pressure transducers to sense flow through the circuit. Once the integrated fluid circuit is plugged into the machine and connected with the machine's components, an operator uses the integrated fluid circuit in a manner similar to the method of using the circuit chamber 230 described above.

As with the air release chamber 230, the rigid body 518 is constructed of a medical grade material. The flexible backing is constructed from a polymer that is flexible and suitable for medical use, such as an elastomer, including silicon elastomers. Other suitable materials include, high and low density poly ethylene, high and low density poly propylene, separately co-extruded mono layers or multiple layers of polyamides, nylons, silicones or other materials commonly known in the art for flexible applications. The backing is attached to the back of the rigid body 518, such as by laser, ultrasonic or RF welding or with an adhesive. In some implementations, the backing is attached so that the edge of each recess is sealed to the backing. Alternatively, the backing is attached only at the edge of the rigid body. If the backing does not seal the recesses from the flat portions, the machine into which the integrated fluid circuit seats is constructed to apply sufficient pressure to keep the fluid flowing through the circuit from leaking out of the recesses and between the backing and the flat surface 520. In the back of the rigid portion 518, ridges can be formed which surround the recesses. The ridges can aid in sealing the flexible membrane to the flat portion 518 when pressure is applied to the circuit.

In some implementations, injection sites 598 are formed at one or more of the recesses. The injection sites 598 can be used to inject drugs or solutions into the fluid. Suitable injection sites 598 are formed of neoprene gaskets into which a needle can be introduced and removed so that the gaskets do not leak or weep after the needle is removed.

Figure 27:
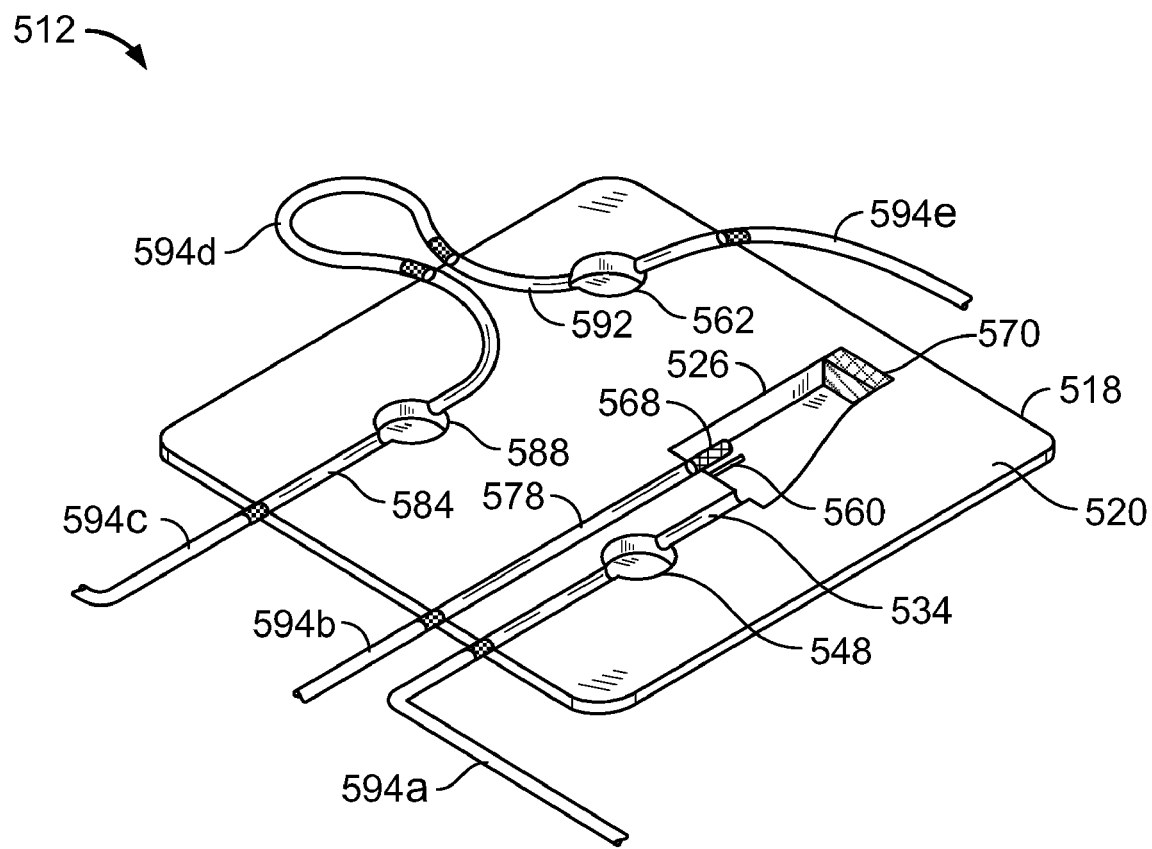
FIG. 27 is a perspective view of the integrated extracorporeal circuit of FIG. 26.

FIG. 27 shows a perspective view of the integrated fluid circuit 512. As in FIG. 20, the flexible membrane has been removed from the integrated fluid circuit 512 to show the recesses.

Using the air release chambers described herein in an extracorporeal blood circuit inhibits (e.g., prevents) air from contacting blood flowing through the circuit Inhibiting air in the chamber can reduce the likelihood of forming clots in the blood. In the event that there is air in the blood before the blood exits the chamber, a hydrophobic micro-porous membrane and a self-sealing vent structure at the top of the chamber allows air that enters the chamber to escape. The membrane and vent structure are part of or connected directly to the air release chamber. This allows the air to easily escape from the liquid filled chamber. Thus, lines need not be connected to the top of the chamber for withdrawing air from the circuit.

The self-sealing vent structure of the vent assembly inhibits (e.g., prevents) moisture or condensation from accumulating on the micro-porous membrane. The micro-porous membrane can lose its ability to vent efficiently if it gets wet. On occasion, the micro-porous membrane can leak due to becoming wet, which may allow blood to escape the chamber. The vent structure of the vent assembly can inhibit (e.g., prevent) the micro-porous membrane from getting wet and leaking blood to the outside of the chamber. In the even that the membrane fails, such as due to a puncture, and fluid passes through to the vent structure, the vent structure swells when it becomes wet. The swollen vent structure inhibits (e.g., prevents) blood from leaking outside of the circuit and into the atmosphere.

The chamber is first filled with saline before being filled with blood. The chamber has a sufficient height so that after the saline and blood are introduced into the chamber, the saline is located near the top of the chamber and the blood is located near the bottom, and little mixing of the two liquids occurs. The saline inhibits (e.g., prevents) most of the proteins in the blood from contacting the micro-porous membrane of the vent assembly at the top of the chamber. If protein accumulates on the micro-porous membrane, the membrane's hydrophobic properties can be inhibited, that is, the membrane can wet, allowing liquid to leak from inside the chamber to outside the chamber. Also, if protein collects on the membrane, the membrane may become inefficient at allowing air to pass through. Thus, a sufficiently long chamber allows the saline to stagnate at the top, inhibiting (e.g., preventing) protein from contacting the membrane.

A dam in the chamber between the entry and exit ports may provide a surface for microbubbles to accumulate. The microbubbles in the blood may then escape through the chamber rather than passing through the exit port. Reducing clot formation and reducing gas in the blood is safer for the patient undergoing hemodialysis. The dam also forces the liquids up into the chamber so that the liquids, and any gases traveling with the liquids, are not immediately pushed out of the chamber before the gas can escape out to the top of the chamber.

Placing components, such as a pocket for taking pressure measurements, channels for fluid flow and the air release chamber, into a single integrated fluid circuit eliminates multiples separate components. Fewer components are easier for an operator to work with and reduce the risk of operator error. The integrated fluid circuit has a rigid side that maintains the integrity of the components, and flexible portions that allow for taking measurements, such as pressure or temperature measurements. Further, the pockets in the integrated circuit eliminate the need for pressure sensing lines in fluid communication with the top of the chamber.

The components described herein can be used with other liquids, such as plasma, water, saline, and other medical fluids. Additionally, liquids other than saline can be used to prime the system. Accordingly, other embodiments are within the scope of the following claims.

What is claimed is:

1. An air-release device for allowing air to be released from a liquid in extracorporeal circuitry, the air-release device comprising:
   an elongate chamber having a bottom region and a top region and a fluid entry port and fluid exit port at or near the bottom region;
   a vent structure at or near the top region of the elongate chamber, the vent structure comprising
   a first porous layer; and
   a second porous layer comprising a porous material capable of swelling when moistened such that the vent structure can inhibit liquid from escaping the air-release device during use; and
   a microporous membrane adjacent the vent structure at or near the top region of the elongate chamber such that liquid can be passed through the elongate chamber from the entry port to the exit port so as to at least partially fill the elongate chamber with the liquid while air exits the chamber via the microporous membrane and the vent structure,
   wherein the first porous layer is disposed between the micro-porous membrane and the second porous layer.

2. The air-release device of claim 1, wherein the vent structure has an average pore size of about 15 microns to about 45 microns.

3. The air-release device of claim 1, wherein the vent structure includes polyethylene, polypropylene or polystyrene.

4. The air-release device of claim 1, wherein the vent structure includes carboxymethylcellulose.

5. The air-release device of claim 1, wherein the vent structure includes a blend of polyethelene and carboxymethylcellulose.

6. The air-release device of claim 1, wherein the vent structure has a thickness greater than a thickness of the micro-porous membrane.

7. The air-release device of claim 1, wherein the micro-porous membrane has an average pore size of about 0.05 microns to about 0.45 microns.

8. The air-release device of claim 1, further comprising a ring into which the micro-porous membrane is press-fit, wherein the ring surrounds the vent structure and retains the vent structure adjacent to the micro-porous membrane.

9. The air-release device of claim 1, wherein the microporous membrane includes a hydrophobic material.

10. The air-release device of claim 1, wherein the first porous layer comprises a porous material capable of swelling when moistened, and the second porous layer is less responsive to moisture than the first porous layer.

11. The air-release device of claim 1, wherein the first porous layer has an average pore size of about 5 microns to about 45 microns.

12. The air-release device of claim 1, wherein the second porous layer has an average pore size of about 15 to about 45 microns.

13. The air-release device of claim 1, wherein the second porous layer has an average pore size that is greater than an average pore size of the first porous layer.

14. The air-release device of claim 1, wherein the second porous layer comprises about 5% to about 50% by weight carboxymethylcellulose.

15. The air-release device of claim 1, wherein the first porous layer comprises about 0% to about 10% carboxymethylcellulose.

16. The air-release device of claim 1, wherein the first porous layer comprises less than 5% carboxymethylcellulose.

17. The air-release device of claim 1, wherein the microporous membrane forms at least a portion of a top surface of the elongate chamber.

18. The air-release device of claim 1, wherein the fluid entry and exit ports are in a bottom surface of the elongate chamber.

19. The air-release device of claim 1, wherein the bottom region of the chamber is flared such that the bottom region is wider than the top region.

20. The air-release device of claim 1, wherein the exit port is substantially vertically aligned with the vent structure during use, and the entry port is horizontally offset from the vent structure during use.

21. The air-release device of claim 1, wherein the chamber has a height of about three inches to about four inches.

22. The air-release device of claim 1, wherein the extracorporeal circuitry is hemodialysis extracorporeal circuitry.

23. A dialysis system, comprising:
a dialysis machine body;
a pump on the machine body;
fluid circuitry in fluid communication with the pump, wherein the pump is configured to push fluid through the circuitry;
an air release device in fluid communication with the fluid circuitry, the air release device being positioned adjacent to the machine body, the air release device comprising
an elongate chamber having a bottom region and a top region and a fluid entry port and fluid exit port at or near the bottom region;
a vent structure at or near the top region of the elongate chamber, the vent structure comprising
a first porous layer; and
a second porous layer comprising a porous material capable of swelling when moistened such that the vent structure can inhibit liquid from escaping the air-release device during use; and
a microporous membrane adjacent the vent structure at or near the top region of the elongate chamber such that liquid can be passed through the elongate chamber from the entry port to the exit port so as to at least partially fill the elongate chamber with the liquid while air exits the chamber via the microporous membrane and the vent structure,
wherein the first porous layer is disposed between the micro-porous membrane and the second porous layer.

* * * * *

UNITED STATES PATENT AND TRADEMARK OFFICE
CERTIFICATE OF CORRECTION

PATENT NO.         : 8,187,466 B2
APPLICATION NO.    : 13/101500
DATED              : May 29, 2012
INVENTOR(S)        : Thomas Irvin Folden It is certified that error appears in the above-identified patent and that said Letters Patent is hereby corrected as shown below:

Claim 5, column 16, line 52:
delete "polythelene" and replace with --polyethylene--.

Signed and Sealed this
Seventh Day of August, 2012

David J. Kappos
*Director of the United States Patent and Trademark Office*